United States Patent
Wiklund

(10) Patent No.: US 6,629,957 B1
(45) Date of Patent: Oct. 7, 2003

(54) PROTECTION FOR PUNCTURE NEEDLES

(76) Inventor: Ernst Sigurd Gustaf Folke Wiklund, Lindevägen 40, Enskede Gård (SE), S-120 48

( * ) Notice: Subject to any disclaimer, the term of this patent is extended or adjusted under 35 U.S.C. 154(b) by 0 days.

(21) Appl. No.: 09/242,512

(22) PCT Filed: May 30, 1997

(86) PCT No.: PCT/SE97/00942

§ 371 (c)(1),
(2), (4) Date: Feb. 17, 1999

(87) PCT Pub. No.: WO97/45152

PCT Pub. Date: Dec. 4, 1997

(30) Foreign Application Priority Data

May 31, 1996 (SE) .............................. 9602141

(51) Int. Cl.[7] .............................................. A61M 5/32
(52) U.S. Cl. .................................................... 604/192
(58) Field of Search ...................... 604/164.01, 164.02, 604/164.05, 164.06, 164.08, 164.11, 165.01, 165.02, 165.03, 165.04, 158, 159, 162, 170.01, 170.02, 171

(56) References Cited

U.S. PATENT DOCUMENTS

| | | | | |
|---|---|---|---|---|
| 5,009,642 A | * | 4/1991 | Sahi | 604/158 |
| 5,030,206 A | * | 7/1991 | Lander | 604/164 |
| 5,066,288 A | * | 11/1991 | Deniega et al. | 604/274 |
| 5,312,345 A | * | 5/1994 | Cole | 604/110 |
| 5,425,718 A | * | 6/1995 | Tay et al. | 604/165 |
| 5,460,611 A | | 10/1995 | Alexander | 604/110 |
| 5,536,257 A | | 7/1996 | Byrne et al. | 604/198 |
| 6,106,499 A | * | 8/2000 | Overton et al. | 604/170.01 |

FOREIGN PATENT DOCUMENTS

| | | |
|---|---|---|
| EP | 0 405 039 A1 | 7/1989 |
| EP | 0 356 810 A2 | 8/1989 |
| EP | 0 657 184 A1 | 12/1994 |
| WO | WO 91/01154 | 2/1991 |
| WO | WO 95/10313 | 4/1995 |

* cited by examiner

*Primary Examiner*—Manuel Mendez
(74) *Attorney, Agent, or Firm*—Winston & Strawn LLP

(57) ABSTRACT

Point protection and method for use at hypodermic puncture needles characterised by that the point protector's active protection function is effected by a thin walled tube that externally or internally is closely fitted to the puncture needle (1) so that a supporting, evenly distributed normal pressure on the thin walled tube arises which substantially increases its capacity to sustain the forces that after accomplished tissue penetration may be expected to affect the protector, without embarrassing deformation, and by that prevent accidental scratch, chafe and/or stab injuries caused by the sharp needle point inclusive tissue damages at punctured tissue for instance at the inside punctured blood vessels, the so-called endothelium.

30 Claims, 12 Drawing Sheets

2.021

2.021
2.011

PROTECTION FOR PUNCTURE NEEDLES

In the medicine of today punctures are daily routine measures. Punctures have many purposes: diagnostic, therapeutic, nutritive etc. Most refer to access to the circulation system for sampling or to establish an intravenous access. The others refer mainly to single injections, which may be intravenous, intramuscular or cutaneous.

At intravenous access the puncture needle has no other task than the establishment itself. The cannula needle is removed when the access is secured. In contrast, the needle has a liquid transport function at sampling and injection.

Common for all used puncture needles is that at least their points must be handled as potentially contaminated, as a stab insult under unlucky circumstances may bring life threatening consequences for affected individuals. Thus, a very urgent need for a well functioning and safe point protection for used puncture needles exists.

Unfortunately proposed solutions of the problem have shown to be rather unsuccessful so far. They have been judged as expensive and/or difficult to use.

WO-A1-9101154 refers to a point protection consisting of a tube-shaped envelope provided with outgrowths that attach to the tissues of the patient and pull the envelope forward to cover the needle point, when the needle is drawn out. Superficially, this may seem to be an elegant problem solution. However, closer scrutiny gives a poorer result.

Contrary to what is said in the publication, the outgrowths will unavoidably increase the patient's discomfort from the puncture. As many patients experience punctures as traumatic even under normal circumstances, this is very unwanted.

More serious is the fact that a design according to the cited publication puts contradictory and unrealistic demands on fit-up and gauging of the envelope and the needle. The fit-up must be firm and the length of movement of the envelope must be sufficient to avoid too early activation of the protection. Simultaneously the envelope must slide easily and the distance must be short not to cause the patient that the firmness of the patients tissues varies and that plastic that is the only realistic material for the envelope varies very much regarding shrinkage etc. and one realises easily that the manufacturing and quality problems become insuperable.

A probable consequence of this is that the function of the protection becomes very haphazard. At the same time the existence of the protection gives the operators a false sense of security. The combination of these facts may increase instead of decrease the frequency of insults.

Another important drawback is that the protection cannot be activated before the needle is drawn out. Beside the mentioned insults caused to the patient by the very shield comes that the needle point after the initial puncture of the vessel wall still is unprotected and may easily cause unwanted insults during the time the handling needs to ensure that the final position is reached.

EP-A1-0356810 refers to a protection consisting of a tube-formed metallic shield or envelope with a blunt end. The protection is activated at the delivery and deactivated by screwing down to press a compressible elastic body together. After use the protection is reactivated by screwing in opposite direction to let the elastic body expand and move the shield forward over the needle point.

Probably protection of this kind will also increase rather than decrease the insult risk as it demands a succession of complicated movements close to the sharp and in the final stage bloody needle. Another serious drawback is that the protection has to remain deactivated, while the needle is put aside, when the puncture area is put in order, if the operator does not have assistance to take care of the needle immediately.

The protection according to this earlier publication differs from puncture needles according to this application by being activated before the use. Thus, its fixation in active position cannot be irreversible.

EP-A1-0657184 refers to a needle point protection consisting of a rod (or a tube) with a blunt end that may be moved forward and backwards within the cannula-formed, sharp-edged needle. In one of the three principally different designs the protection it is activated at delivery and deactivated by pressing two wings together at the use. The handling of the needle is complicated by the deactivation arrangement. The protection is reversible and the risk large that the combination of needle and protector at handling after use may get jammed so that the activation is neutralised. Thus, this type of protection implies a false security that may lead to carelessness at the handling of the dangerous waste that used needles are and in this way increase the insult risk.

In another design, which can be used for injection syringes only, the rod has a double function and serves simultaneously as an injection plunger. Of course, this will imply important limitations upon injected volume. In this design the protection activation may be made irreversible. The double function as injection plunger implies that only a solid rod can be used. In this way this earlier publication differs from this application that refers to designs with thin walled tubes or hoses.

In a third design, intended for the placing of catheters, the protective rod is fastened to a body that has an elongated projecting impact part at its opposite end. At activation this impact part is struck against a hard surface to bring the protective rod forward to an irreversible protective position. The activation requires 1. Removal of the needle body, 2. Turning of the needle body, which probably requires grip changing, 3. A comparatively hard stroke against a suitable surface. Probably all this must wait until the operator has put the puncture area in order and has both hands free. During this time the needle will be lying unprotected. The activation demands handling close to the needle point. Again a protection of this kind may be expected to increase rather than decrease the injury risk by that a) the existence of protection gives a false sense of security when the protection activation becomes haphazard, b) the handling close to the needle point increases the risk that the operator under stressed conditions misses and injures her or his own hand.

The inventor behind this application has experience of many years of emergency treatment of different kinds and has, guided by this experience, compiled the following demand profile of functioning hypodermic needle protection.

1. The activation of the protective function should not require more work and/or more time as the work situation is characterised by hustle and stress already.
2. If the activation is voluntary it should be a natural part moment that does not require any special attention.
3. Adding of the protective function to the equipment should not require design changes that make changing of habitual grips and handling routines necessary.
4. Use of equipment with built in protective function should not cause more discomfort for the patient than that which is unavoidable due to the puncture itself.
5. The activation should not require hand grip in front of or close to potentially contaminated needle points.

6. Activation of the protective function should be possible latest in the stage, when the needle is drawn out, i.e. before the operator has to put the puncture needle with accessories away to take care of the putting the puncture area in order.

To these very strong "should" a couple of weaker but important ones have been added.
1. Activating should be possible without grip change.
2. For liquid transport needles that are not protected by outside cannulae activation should be possible in the initial stage already, i.e. when the vessel puncture has been carried through to prevent inside injuries at the vessel walls.
3. Reasonable safety for, largely seen, one-hundred per cent, irreversible activation should exist, as otherwise the same strict routines as before have to be applied.

None of the earlier proposed solutions come near of fulfilling this demand profile.

At the working out of this invention the demand profile has been guiding. The invention starts from a simple, elementary and easily understood principle. Instead of loose accessories, which seldom or with difficulty may be put in place without both hands, a built-in point barrier in the used equipment is proposed. A well known and painful experience exists that desirable and available protective arrangements often remain unused due to troublesome application procedures.

The point protection of the invention consists of a thin-walled tube or a thin walled hose of suitable length fitted outside or inside the puncture needle and automatically or manually movable, with hand grips at safe distance from the needle point, from a not activated rest position to an activated, irreversible protective position, where the front end of the protector is fixed a few millimetres in front of the needle point to eliminate the risk of stab or scratch injuries from the sharp needle point.

That the handling shall be possible at safe distance from the needle point and potentially contaminated parts shall be interpreted in the way that under no circumstances the handling shall have to be done so it brings the hand in front of the needle. Instead the grip point should lie clearly behind the part of the needle that has been inside the patient's tissues and thus is potentially contaminated. Further the hand grips for activation should be such that possible fumblingness or slipping does not bring the hand in front of the needle point.

It should be noted that a protector according to this invention, which does not use the patient's own tissues for protection activation, must be pushed forward over the needle point by a force applied from behind. This in contrast to the protection according to WO-A1-9101154, which is drawn forward by a force caused by the outgrowths attaching to the patient's tissues and causing a pulling force applied at the front part of the needle protection.

That the tube (or hose) is thin walled means that its wall thickness is smaller than its inner diameter. The wall thickness becomes of course dependent of the needle diameter and the material chosen for the protector. For very rigid materials, such as stainless steel, a wall thickness of ~0,01 mm may be quite sufficient. For plastic material larger wall thickness may be required, for instance 1 to 2 mm and for very thick needles even up to 3 mm. In the cases where the muzzle end of the protector is used for the fixation of the irreversible protective position a local wall thickening of up to 2 mm or more may show to be appropriate even for thin needles.

The point protector is at delivery mounted upon the needle in what is called rest position in this description. This rest position is chosen so that use and function does not get obstructed. Fixation to protective position must be adequate and may be controlled either by a suitable arrangement at the surface of puncture needle itself or at the surface of the needle body. Another possibility is fixation backwards with the aid of the front end of the needle and forward by a stocking of suitable length.

A reliable mechanical point protector is a fundamental prerequisite for protection against serious contagious inoculation. Added to this comes the desideratum to avoid exposure of contaminated surfaces for touching when taking care of the needle after finished use.

This desideratum is easiest to fulfil for the puncture needles for intravenous access. This will be obvious from the following description of different embodiments of the basic idea.

For other equipment categories special arrangements, described below, are required.

Figure 20:
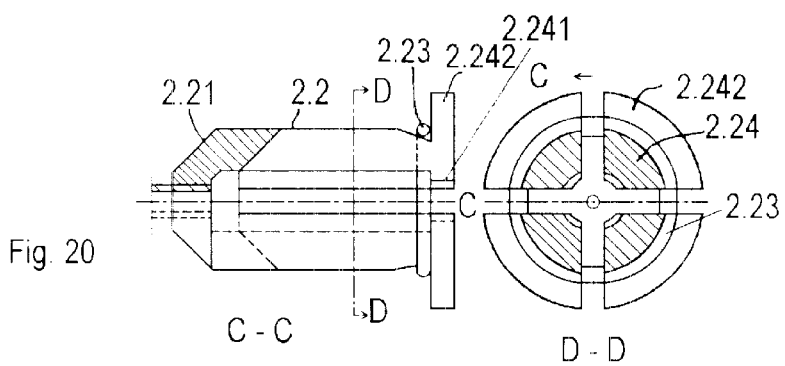

FIG. 20 shows a point protector with its resilient elastic O-ring 2.23 ready to be threaded on the needle 1 and the needle body 1.3. The body 2.2 of the protector fixes, by its disc-shaped circular part 2.21, the thin walled tube 2.0 and is at its rear part divided into four cylindrical quadrants fitting to the four wings of the needle body.

Figure 21:
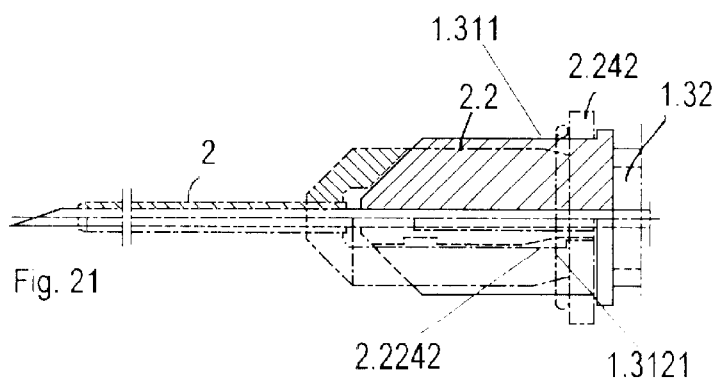

FIG. 21 shows the point protector of FIG. 20 with threaded needle and needle body and the somewhat projecting wings 1.311 and the point protector in rest position.

Figure 22:
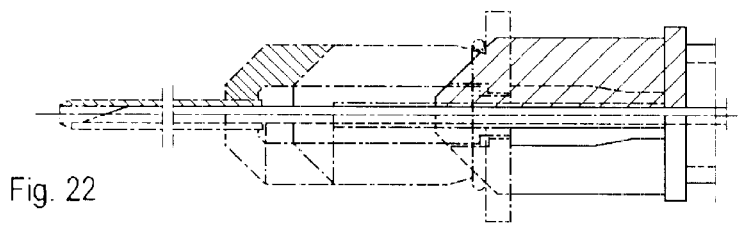

FIG. 22 shows the point protector of FIG. 20 in protective position.

Figure 23:
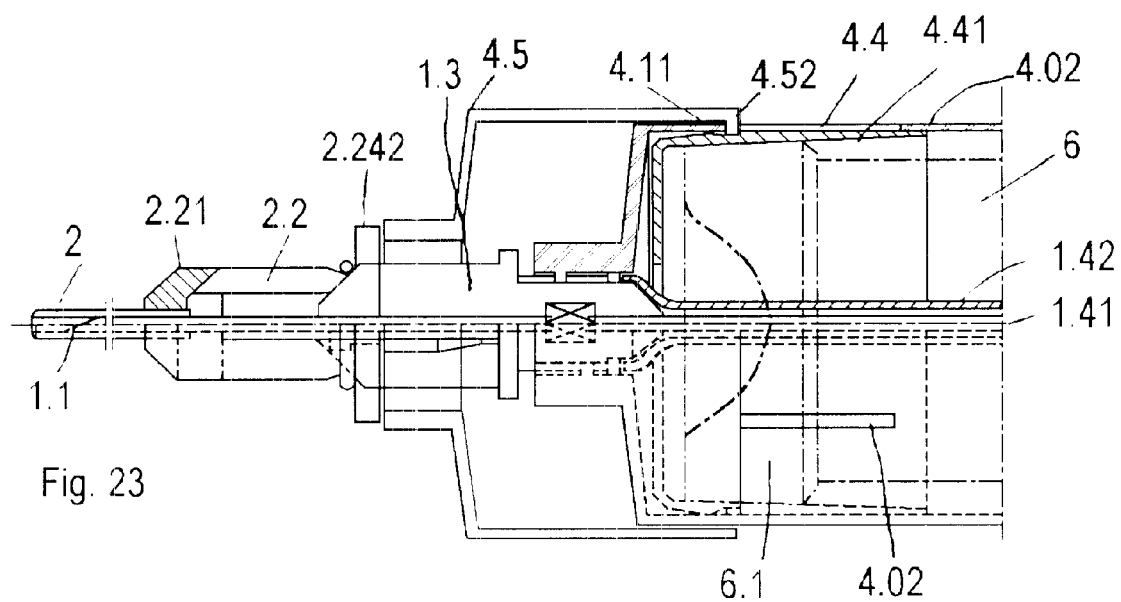

FIG. 23 shows a proposed arrangement to activate the point protection automatically with the aid of an external driving sleeve at the final positioning of the test tube.

Figure 24:
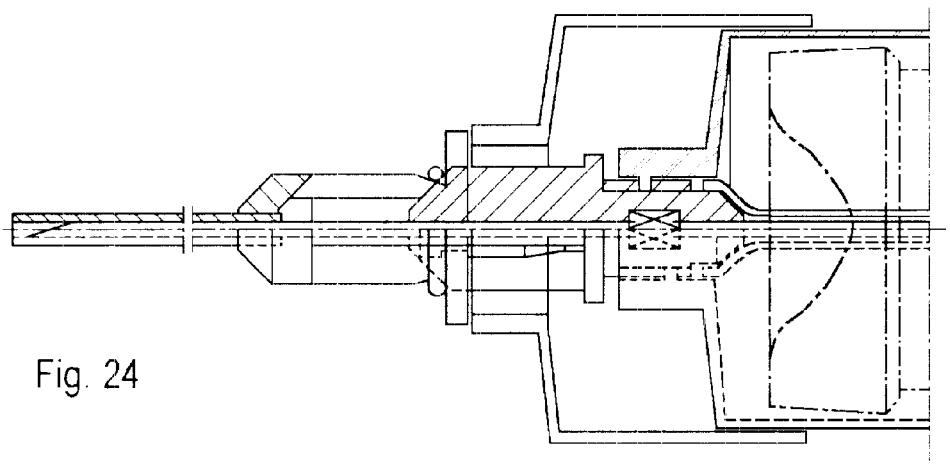

FIG. 24 shows a corresponding arrangement without automatic activation.

Figure 25:
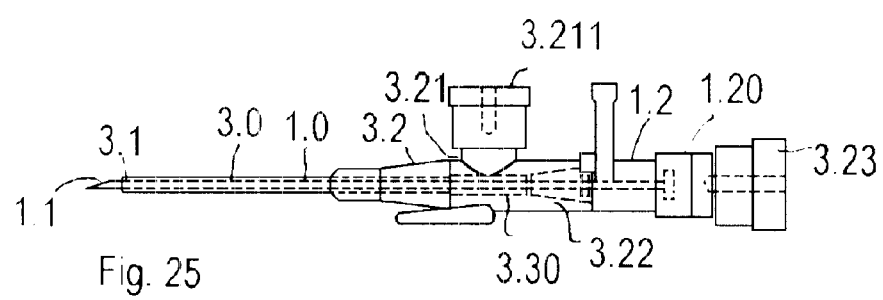

FIG. 25 shows a common version of equipment for peripheral, intravenous access.

Figure 26:
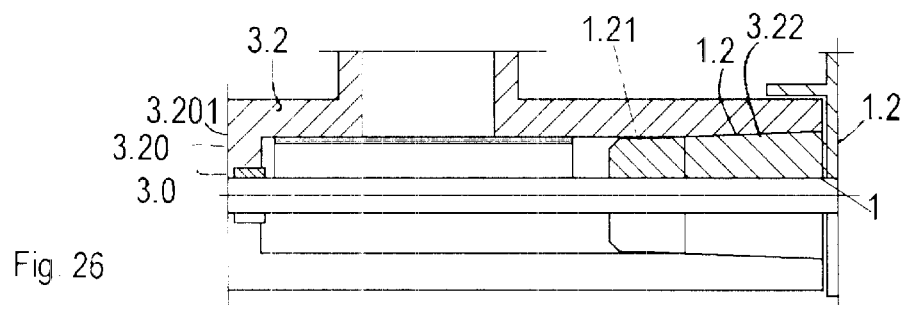

FIG. 26 shows details of FIG. 25 in larger scale.

Figure 27:
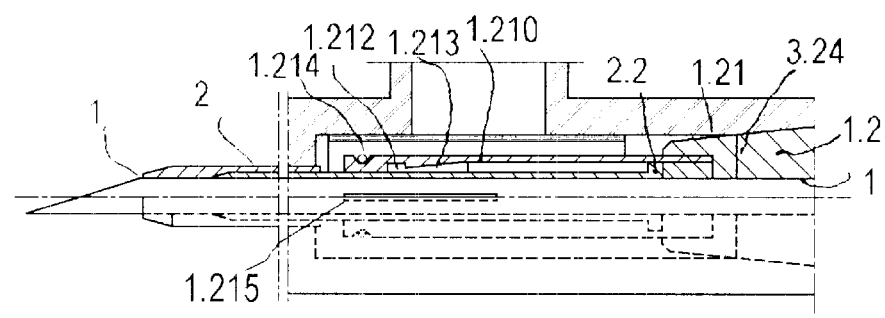

FIG. 27 shows a point protector for puncture needles for peripheral, intravenous access. The protection is activated automatically, when the cannula is advanced and the needle retracted. The protective tube is lying under the access cannula, when the puncture is done. When the cannula is advanced at stationary needle the protector follows as far as the limitation and fixation arrangement in the chamber of the cannula body so allows and locks then the protective tube in activated protective position, possibly completed first after that the needle has started being retracted, and follows then the needle out.

Figure 28:
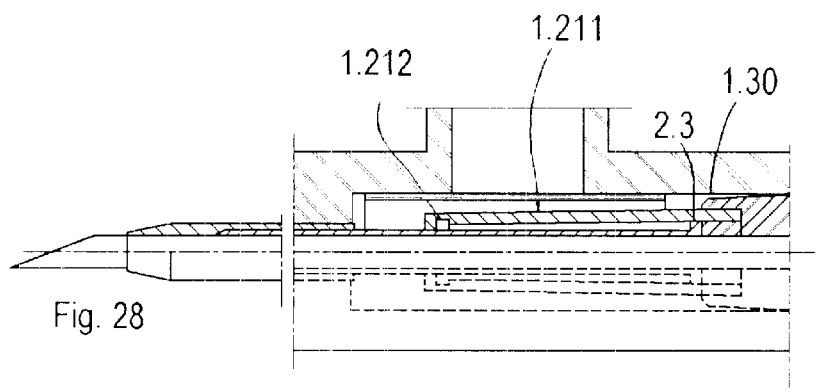

FIG. 28 shows another design of the fixation and drive arrangement.

Figure 29:
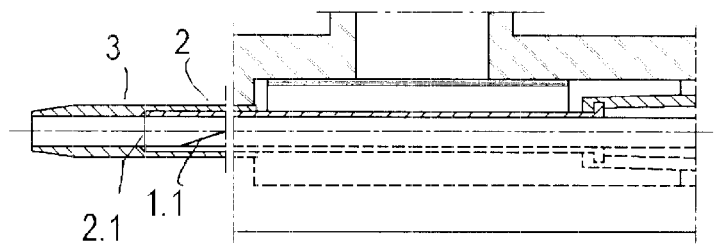

FIG. 29 shows the protector of FIG. 27 and FIG. 28 in activated protective position.

Figure 30:
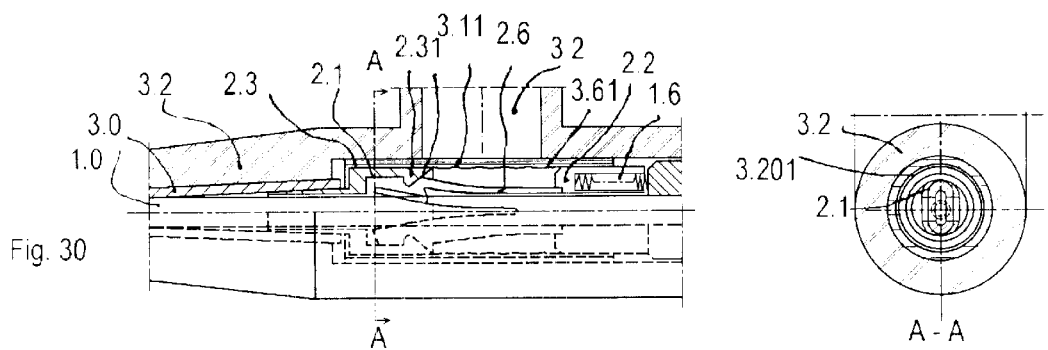
Figure 31:
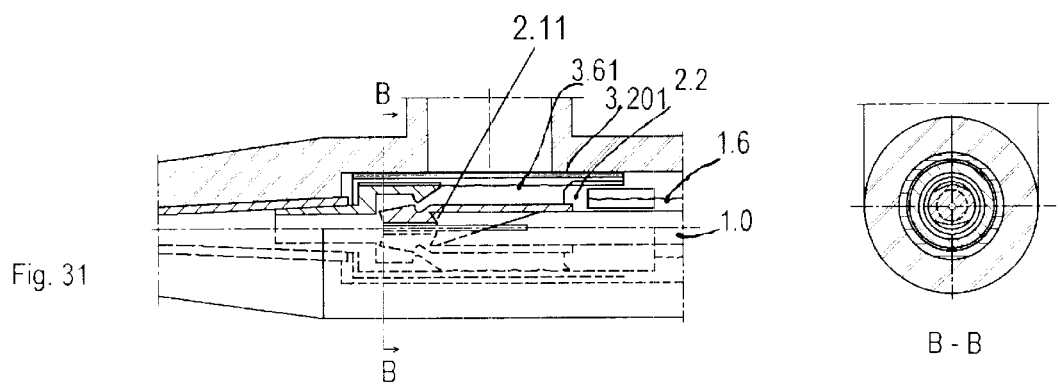

FIGS. 30 and 31 show a point protection that to its largest part can be accommodated in the chamber 3.20 of the cannula body and kept there by a sleeve 2.3, until a foldable thin stocking 1.6 meters up a suitable length for the activation of the point protection. When the whole point has passed the barrier border 2.11, the two halves of the protector strike together, owing to their inherent elasticity, at which the stocking 1.6 dislodges the activated needle protection 2 and with the aid of another stocking the sleeve 2.3. The protector and sleeve follow the needle, when it leaves the cannula body entirely.

Figure 32:
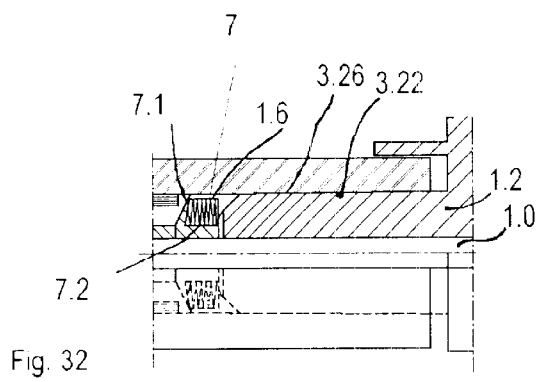

FIG. 32 shows details of a retaining disc 7 with a length limiting, folded stocking 1.6 fastened at the needle body. The disc 7 should be fixed to the protector 2 if it either lacks own capacity for recognising the active position of the needle or is not able to limit its forward movement at the needle when it is retracted.

Figure 33:
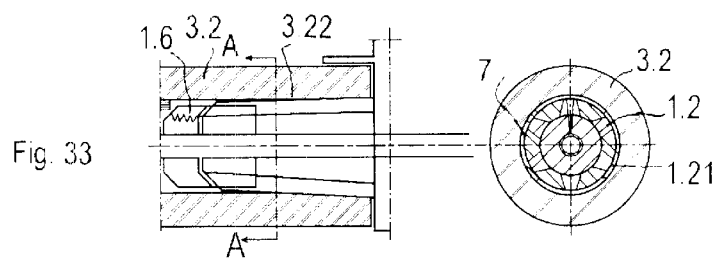

FIG. 33 shows details of the conical front part of the needle body.

Figure 34:
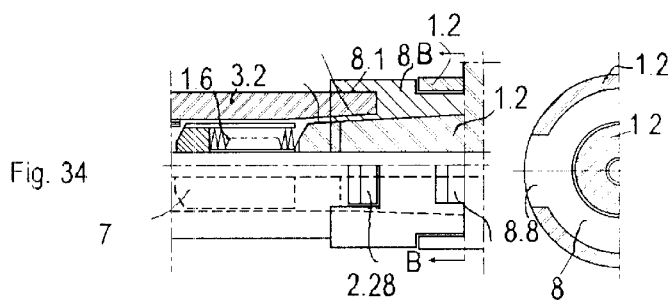

FIG. 34 shows an extenuation of the disposable space in the cannula chamber 3.20 by an adapter.

Figure 35:
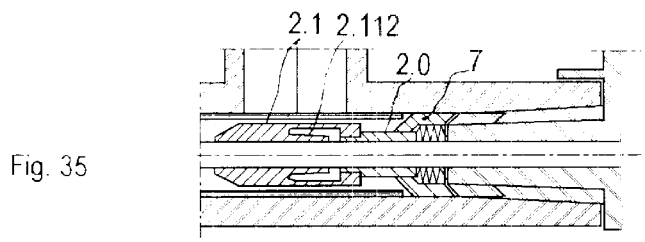

FIG. 35 shows a design with the retaining disc 7 fixed to a point protector 2, which is provided with an anterior, entirely rotation-symmetrical, fixation arrangement 2.1. The posterior part 2.112 of the fixation arrangement 2.1 is in its non-active position extended to a cylindrical form which surrounds the needle.

Figure 36:
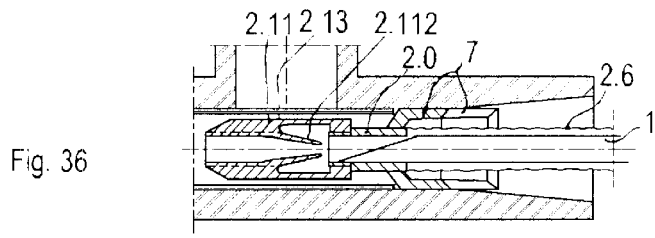

FIG. 36 shows the same arrangement as FIG. 35 in the moment during the needle retraction, when the length limiting stocking 2.6 starts acting upon the retaining disc 7 with a backwards directed disengaging force. By that an elastic extension of the stocking 2.6 occurs. This extension is adjusted so that the relaxation, when the disc 7 gets loose, moves the protector backwards at the needle so that the needle point is caught by the now conical rear part 2.112 so that the protector reaches its fixed active position.

Figures 37, 38:
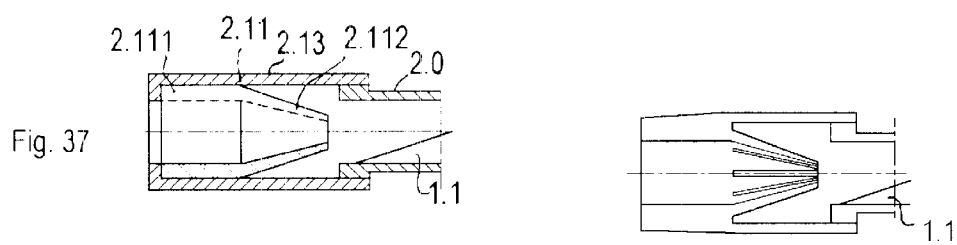

FIG. 37 shows a design of the muzzle part 2.1 constructed of an elastic inner part 2.11 and a rigid outer part 2.13.

FIG. 38 shows a design of the muzzle part in for instance polypropylene 2.1. This design with longitudinal slits in the part 2.112 can be injection moulded in one piece.

Figure 39:
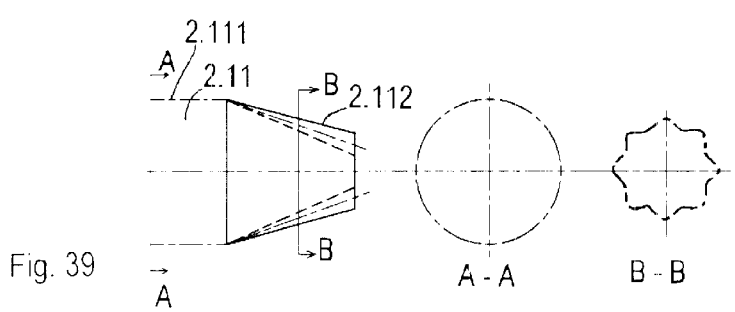

FIG. 39 shows a muzzle part 2.11 with longitudinal soft corrugation in the conical part. The muzzle part, which is shown in activated position, can be injection moulded in one piece.

FIGS. 40, 41, 42 and 43 show a variant of the point protectors of FIGS. 30 and 31 with improved protection against break through of the protective barrier.

Figure 44:
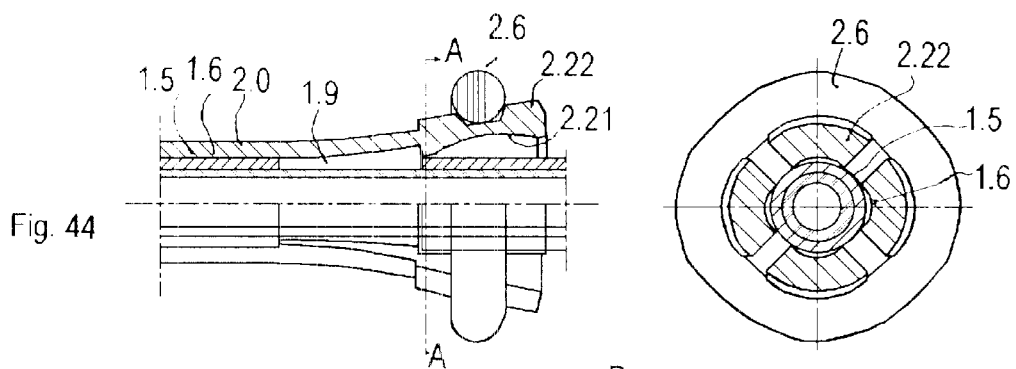
Figure 45:
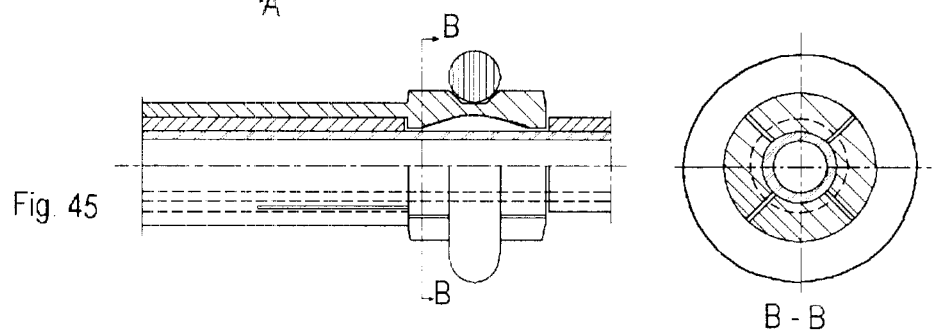

FIGS. 44 and 45 show a design alternative, where the point protection can be accommodated in the cannula chamber 3.20 in non-active condition and kept there by a simplified arrangement 7, according to FIG. 32 and activated by that the protector 2 itself recognises a change in the needle's surface that activates and fixes the protector against forward and backwards directed dislocation forces of reasonable strength and by that can set free the retainer 7, when the protective position has been reached. The need for the stocking 1.6 is eliminated. As it is important that the change in the surface does not bring with it perforation of the needle or a too large weakening of its bending resistance a circularly running groove, ~0,05–0,1 mm deep is proposed, produced by that the needle is constructed of two concentric tubes 1.5 and 1.6, of which the outer one is divided into two parts drawn apart so that a gap 1.9 forms the desired groove. This groove may in certain cases be closed at start position and opened automatically at a suitable time during the activation stage of the protection.

Figure 46:
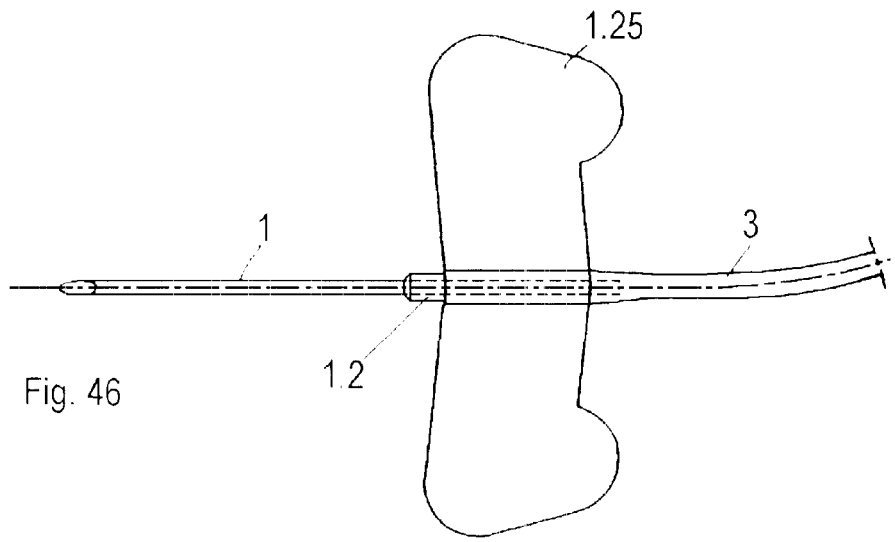

FIG. 46 shows an existing common design of a butterfly needle.

Figure 47:
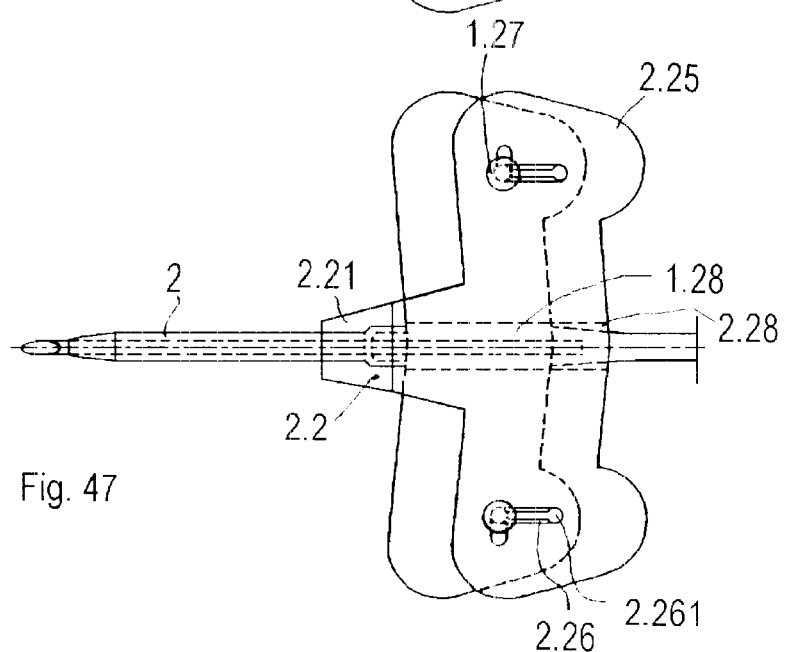
Figure 48:
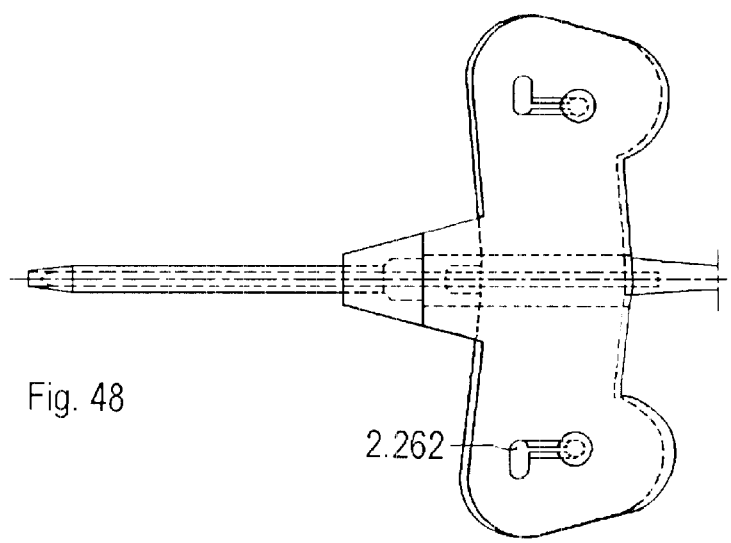

FIGS. 47 and 48 show a proposed completion with point protection according to the invention.

Figure 49:
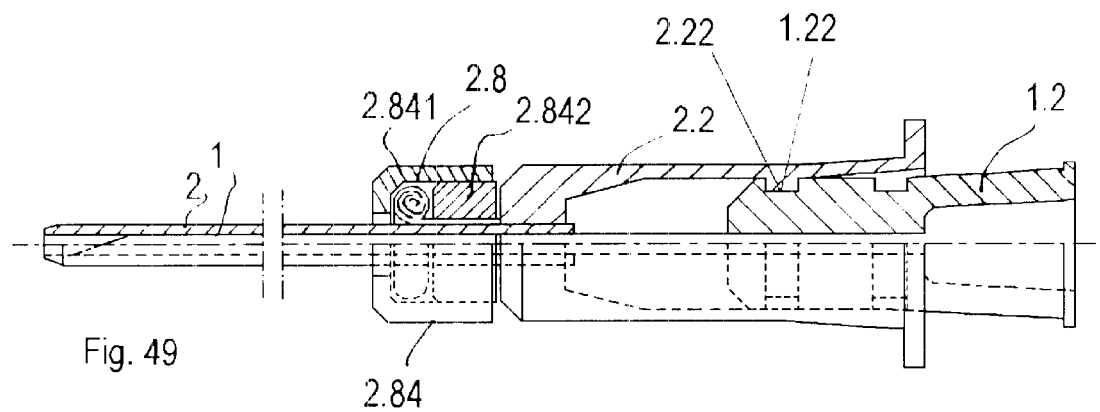
Figure 50:
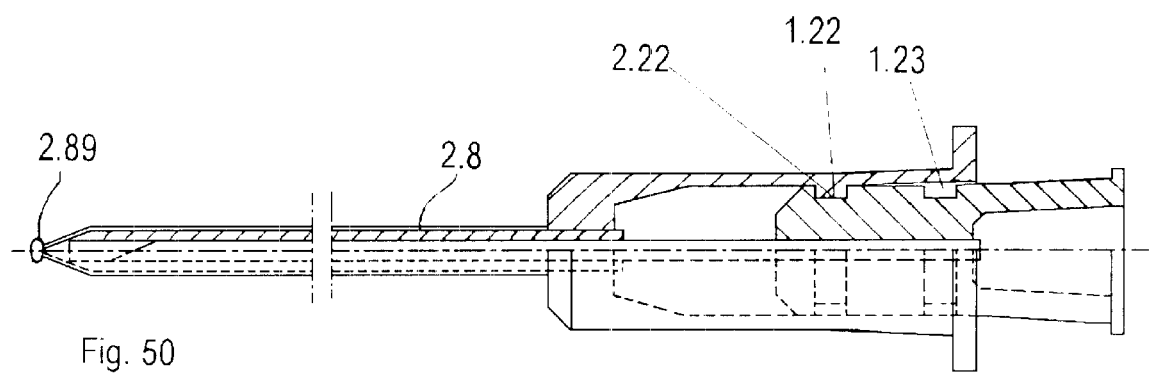

FIGS. 49 and 50 show a simple arrangement to cover potentially contagious parts of the point protection with an uncoiling stocking.

FIGS. 51, 52, 53 and 54 show an arrangement for the turning of potentially contagious parts of the point protector inside out at the needle retraction.

Figure 1:
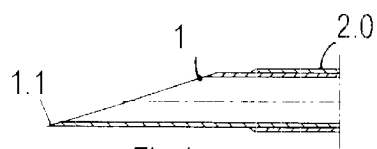
FIGS. 1 and 2 show front ends of an injection needle provided with a point protector in rest position.
Figure 2:
Figure 3:
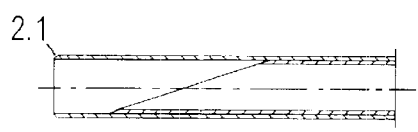
FIGS. 3 and 4 show front parts of an injection needle provided with a point protector in protective position.
Figure 4:
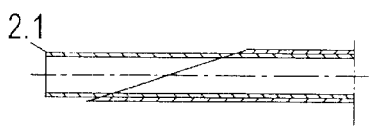
Figure 5:
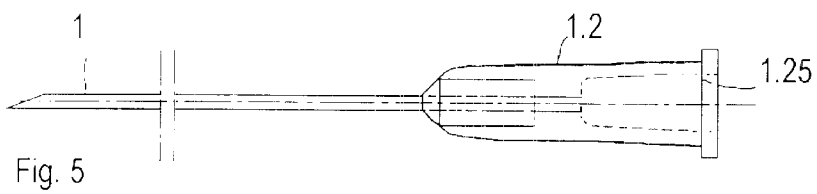
FIGS. 5 shows a common injection needle.

The FIGS. 1 and 3 show the principle of point protection according to the invention in rest respectively protective position if an outside thin walled tube is chosen. The arrangement gives a surprisingly efficient stiffening of an otherwise little resistant protection tube for instance of cannula material. This is under the condition that the fitting is tight and accurate and that the projecting tube length in the protective position is suitable.

In the FIGS. 1 is a puncture needle with a needle body 1.2 that at the back is designed as a Luer cone 1.25. The point of the puncture needle is designated by 1.1. In the same way 2 stands for the point protector, 2.2 for the point protector body and 2.1 for the front end of the point protector. Other designations will be obvious from the description. (Luer cone is an in the medicine common designation for a standardised tightening combination of female and male connections for liquid and gaseous media).

Figure 6:
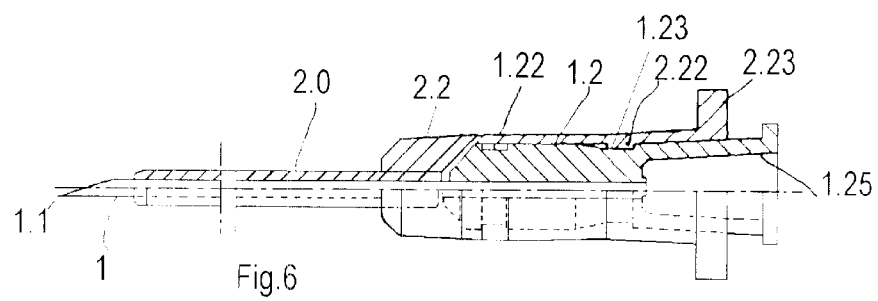
FIGS. 6 and 7 show a modified injection needle for manual activation with a point protector in rest position and protective position.
Figure 7:
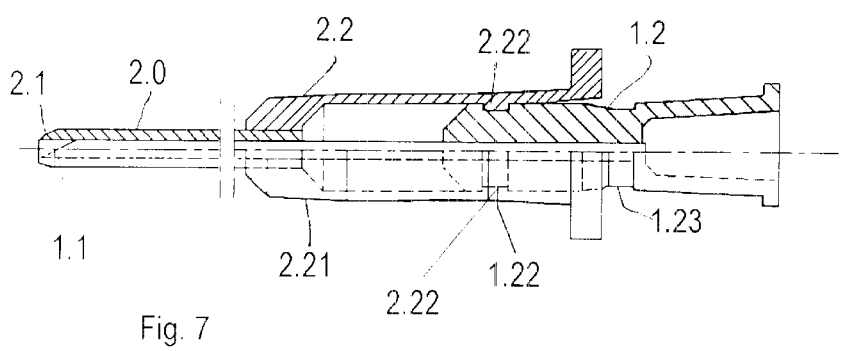

In FIG. 6 a point protector according to the invention is shown. The needle body 1.2 with unchanged Luer cone 1.25 is elongated at the back to fit the body 2.2 of the point protector 2. It is provided with an internal, circular shoulder 2.22 with sharp edged rectangular section fitting to the corresponding grooves 1.23 respectively 1.22 in the needle body 1.2. In this way the protector gets two well-defined positions. The rear position, the rest position, has been designed to allow movement forward of the protector 2 by a forward directed force on the flange 2.23 of the protection body. The forward movement is limited by the anterior groove 1.22 of the needle body where the shoulder 2.22 is fixed irreversibly, which is shown in FIG. 7. The position of the needle point appears from FIG. 3, too. It has been found that even a thin walled protection tube of polymeric material of corresponding kind as the one used for cannulae for intravenous access gives satisfactory mechanical point protection. To this end the support from the enclosed needle and suitable length of the projecting part of the protection contributes.

As needles at delivery are usually enclosed in a protection sleeve the anterior 2.21 of the protection body 2.2 is designed with the standardised Luer conicity so that a corresponding protection sleeve may be used.

Figure 14:
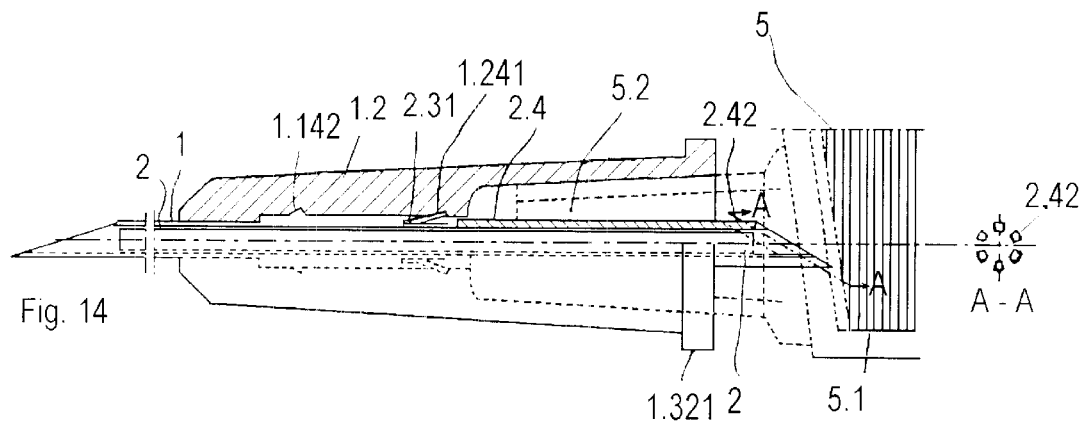
FIG. 14 shows an injection needle, with a point protector in rest position, adapted for automatic activation of the point protection with the aid of the injection plunger.

Usually external protection alternatives according to FIGS. 1 and 3 are to be preferred, especially if the needle with an unchanged diameter has to transport a large flow volume. However, an internal design alternative may sometimes offer advantages, especially because this alternative makes simple, automatic activation, governed by the end position of the syringe plunger, possible. FIG. 14 shows an example.

Figure 11:
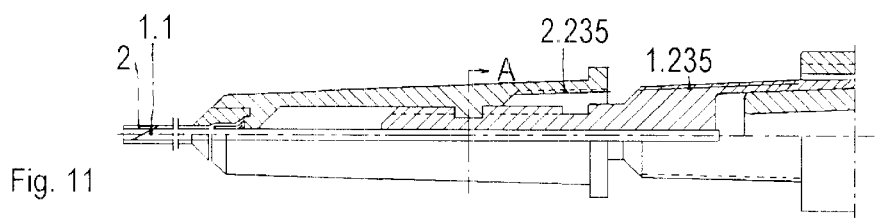

The front part of the protector should be extremely thin walled, <0,05 mm, i.e. preferably of stainless steel to decrease the encroachment in the flow area. The rear part of the protection shall contain a fixed socket 2.31, which with the aid of grooves 1.241 and 1.242 at the inside of the needle body defines and fixes the rest and protective positions of the point protector in relation to the needle. The rear part of the point protector is enclosed by a stiffening and elongating tube 2.4 of suitable material, for instance plastic, with suitable modul of elasticity. This elongating tube may easily be moved backwards, but must offer suitable resistance in forward direction. This telescope function is obtained by dose fitting combined with suitable surface structure. In this way a stabile adjustment of the back end of the elongation tube 2.4 to a position, where the plunger 5.1 of the syringe 5 at the end of the emptying stage can, by way of the elongation tube, move the protective tube 2 from its rest position to the protective position, where it is fixed by the groove 1.242, is made possible. If one, at the adjustment of the elongation tube 2.4, has overestimated its desired motion distance, so that the protective position is reached before the plunger 5.1 has reached its bottom position, the front stop of the elongating tube 2.4 in relation to the protective tube 2 should yield, without that the fixation in protective position 1.242 gets dislodged. The back end of the elongating tube 2.4 should be designed with a "crenellation" 2.42 and be bevel cut to ease the application of needle plus protector at the syringe, which often has a narrow point entry, and in spite of the contact with the underside of the plunger maintain free flow passage. FIG. 14 shows just the situation with the protector 2 in rest position. In protective position the picture will be analogous with FIG. 11, i.e. the fixation sleeve 2.31 has been moved to the anterior groove 1.242 of the needle body 1.2.

It should be noted that tendencies of air containment may appear at the design of FIG. 14. Sharp attention should be observed until the use has developed to routine. A special design of the underside of the plunger may be desirable.

Figure 15:
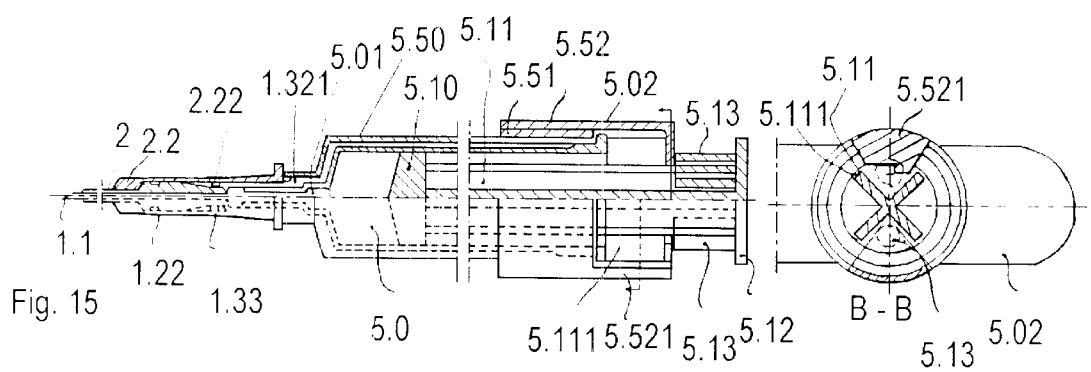
FIG. 15 shows an injection needle, with a point protector in rest position, with attachments for automatic activation aided by the pump rod of the syringe.

The external version of point protection for hypodermic needles causes larger problems with respect to automatic activation. FIG. 15 shows one of several possible alternative. Concerning point protector arrangement and needle body and their detailed designation FIGS. 6 and 7 are referred to. In FIG. 15 the syringe body is provided with an external in axial direction movable driver 5.50, in front designed with a tapering cylindrical part with a fore edge designed for moving the protector body 2.2 from its rest position to a fixed protective position, see FIG. 7!

FIG. 15 and FIG. 14 is simplified by that a preferred external lock arrangement, so called "Luer-lock", for the somewhat oval rear flange 1.321 of the needle body is omitted for plainness reasons. Design according to ISO 594-2 or similar is preferred. Such a locking device at the needle body eliminates the risk that the needle body comes loose at the conical fit between needle body and syringe without requiring complicated handling at application and removal.

The movement of the driver 5.50 is limited backwards by the rear flange 5.0 of the syringe body, which at both sides form a finger plate 5.02 fitted to the insides of the index and middle finger, while the thumb of the operator presses against the press-plate 5.12 at the rear end of the plunger rod 5.11. The anterior part of the driver is constructed of an inner, shorter distance cylinder 5.51 and an outer part consisting of first a cylinder of the same length as the distance cylinder, after that elongated and cut, so that it with moderate negative tolerance straddles the oval finger plate 5.02 and after that is bent to a cut circle sector pair 5.521 that are contact elements to the plunger rod 5.11. The contact between the plunger rod 5.11 and the driver may be fixed at an arbitrary stage of the plunger movement with the aid of a turning ~45° C. clockwise of the, in section, cross-shaped plunger rod 5.11. The fixation is adjusted so that the plunger movement, without too much force, may continue to the bottom position even if the driver 5.50 has reached its active position, i.e. when the sectors 5.521 has reached the back side of the syringe body.

The plunger rod has also a contact element independent of its border surfaces 5.111, namely the tube pair 5.13. This is to safeguard an active position for the point protector, when the plunger 5.10 has reached its bottom position. Thus, the point protection will be activated, even if the operator has refrained from or overlooked the possibility of early point protection activation, when the puncture has been carried out and the needle has reached its desired intravasal position. The operator determines this position routinely by the turning of the finger position between the plates 5.12 and 5.02 so that one gets blood aspiration showing at the anterior part of the syringe. This movement may be a suitable mnemotechnical coupling to the turning movement needed for early activation. The action implies a much more lenient contact with the endothelium of the vessel wall than even the most careful handling of a sharpened needle point.

The tube pair 5.13 must be designed so that it safeguards a point protector activation in the end position of the plunger and allows a rest position for the protector, when the needle is attached, even if the plunger is at its bottom position. This is possible if the tubes are elastic so that they can be squeezed together to allow passage of the sector formed stop surfaces 5.521. Such squeezing together is suitably effected by a thumb forefinger grip at the middle of the tube length, axially seen. Of this follows that it is desirable that at least the outer half tube wall is resistant against bending in axial direction, so that the squeezing together results in a release for passage of the ends of the tubes past the sector formed stop surfaces 5.521. This can be brought about for instance by dividing the tube wall into axially running ribs with a sufficient moment of inertia against axial bending. It may be desirable that the passage remains open a few seconds and after that is getting back to the start position. Retardation may be obtained by that the ends of the tubes 5.13 are made gas-tight and provided with a direction-control flow opening of type non-return valves. Then the ends should have a concave-dished design. Several possibilities exist to bring about the reversible stop function that for reasons of simplicity has been illustrated as cylindrical tubes. One may instead, inter alia, chose a conical form that either springs away or lifts away the stop sectors 5.521 by a counter clockwise turning of the plunger rod 5.11.

So far examples of technical solutions for activation of the point protector according to this idea. Several other possibilities are possible. A review of the essential moment of the injection procedure is therefore justified.

The procedure begins with the so-called drawing up, i.e. filling the syringe with the intended amount of the prescribed substance. This is usually done by a special drawing up needle with considerably a larger diameter than the puncture needle to increase the velocity of flow.

When intended substance quantity has been "aspired" the drawing up needle is replaced by the puncture needle with its point protector in rest position. (The drawing up needle has not had tissue contact and has not to be regarded as potentially contaminated and in need of injury protection). At the attachment of the puncture needle one must control that the driver 5.50 is sufficiently retracted not to dislodge the position of the point protector position at the needle (In the described arrangement this condition is fulfilled). When the puncture needle with its protector has been attached, syringe and needle must be freed from all gas inclusions. This is routinely done by that the operator with the needle turned up carefully advances the plunger until nothing but gas free liquid leaves the needle.

The puncture, which now is nearby, requires new finger setting at the syringe body and in some moment help with the other hand. After sterile washing of the skin, skin penetration and puncture of the vessel wall the point position and the contact with the blood vessel must be controlled. The control is done by careful aspiration with the aid of the plunger, so that the position of the point is not moved to slip out of the vessel or perforate the vessel wall from the inside. When the operator, possibly after position adjustment, can observe a satisfactory colour change in the front content of the syringe it is time for a careful beginning of the injection, at which one puts intense attention to unwelcome indications of extravasal injection flow, in which case a renewed puncture effort has to be done.

The wish to get, so far possible, an automatic activation of the point protector during an early stage of the injection is helped by a suitable ergonomic design of the grip surfaces combined with a natural integration of the tempo routine at the required grip changes. A professional ergonomic planning and standardised training of operators can be expected to solve the problems satisfactorily.

Now some words about the manufacturing technique of the driver 5.50. In FIG. 15 a construction in three parts 5.50, 5.51, and 5.52 is shown schematically to illustrate the described function. This construction is little adapted to rational mass production. First hand the parts 5.50 and 5.51 may be moulded in one piece to be, at mounting, threaded on the syringe body 5.0 from the front. The part 5.51 should then be given a design that allows threading on of 5.52 from the back inclusive passage of the sector surfaces 5.521 past the plunger rod 5.11 and after that an irreversible fixation to 5.51. Maybe one has to accept that the part 5.52 is divided in two identical halves or also that one refrains from the pair and is satisfied by just one of the stop surfaces 5.521 shown.

Early activation, to spare the vessel wall, is also possible for the internal alternative according to FIG. 14 and can be done by advancing the contact between the plunger 5.1 and the elongation tube 2.4. One may then begin by elongation the protection arrangement maximally before attaching needle and point-protector at the syringe. Then one must be aware of the risk for an irreversible activation position if the back end of 4.42 is pushed too far before the puncture is done.

As is obvious from the described designs the automatic activation of the point protector causes additional costs. Are those really justified? At these considerations the set of problems must not be simplified right to that it should lie entirely in the operator's own interest to carry through a voluntary activation step. It does not concern just the operator's own protection, indeed. An unprotected needle point is a common risk for the entire nursing environment, until the needle has reached the destruction oven. Before this it has passed several handling stages and been a collective safety risk.

Earlier the importance of an ergonomically easily accepted activation procedure to ensure use of the protection has been pointed out. By preference it should be understood as a reflex movement coupled to the retraction of the puncture needle from the patient's tissues or still better as a marking that the injection can begin.

The described arrangement implies that the attachment of the needle material at the syringe requires almost identical thumb/finger movements as the point protection activation. The arrangement is a development of the trains of thought behind FIG. 6 and FIG. 7. The acceptance of a voluntary activation movement implies an appreciably simplified manufacturing and thus reduced cost of the protection. FIGS. 8 to 10 and FIGS. 11 to 13 describe the arrangement. For reason of space just the Luer lock part of the syringe is shown. The usual, well-known protection sleeve has been totally excluded.

Figure 8:
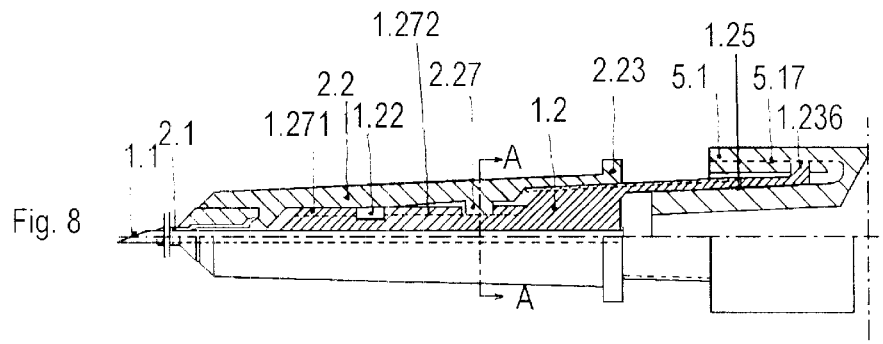
FIGS. 8 to 10 and FIGS. 11 to 13 show in detail a suitable way to bring about the manual activation.
Figure 9:
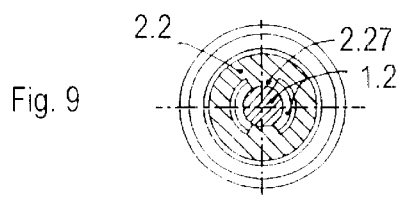

Needle 1 with its point protector 2 in rest position and protected by a standard sleeve is proposed to be supplied in sterile packing as disposable material. In FIG. 8 the puncture equipment with the point protector in rest position is shown. The protection body 2.2 is threaded on the front part of the needle body 1.2 with a conical fit of the protector's contact surface 2.235 to the corresponding surface of the needle body 1.235. Both surfaces are proposed to be structured with an axially running knurling to allow transmission of torsion moment from an external grip of the protection body 2.2 to the Luer lock part of the needle body. This torsion moment will give acceptable security to the Luer lock fixation to the syringe 5. The grip between the surfaces 1.235 and 2.235 are strengthened if the thumb/finger grip of the protection body is given a content of a backwards directed axial component. To this is added that the protection body is provided with two diametrically situated weakly tapering drivers 2.27 adapted to an external groove system 1.272 and 1.271 and 1.22. The groove 1.272 starts from a back end position 1.273 with a relatively short axial distance and has then a helical course under about 180° turning to open itself in the somewhat deeper equatorially 360° running groove 1.22. It is intended to fix the protector in its activated position. More about that later, now back to the rest situation with the drivers close to the end position 1.273 of the groove 1.272.

Figure 10:
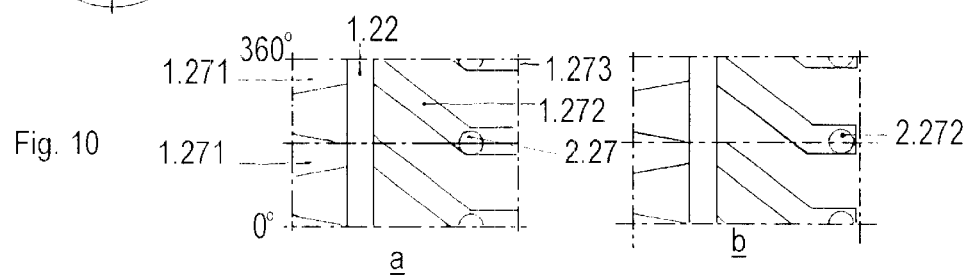

FIG. 10 with part figures a and b show a spreading in plane of the cylindrical anterior part of the needle body 1.2. As the tolerance range of the contact surfaces 1.235/2.235 may allow some variation of the protection body axial position the outer positions of the drivers 2.27 are shown in drawing 10. It is obvious from the figures that if the drivers are situated between these positions they can transmit an appreciable torsion moment in desired direction.

Figure 13:
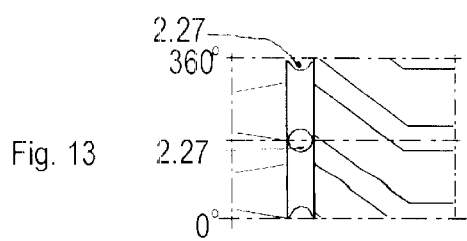

At interpreting of FIG. 10 and FIG. 13 one should note that—seen from the front—a clockwise torsion moment at the protection body can be illustrated by a force directed downwards from the drivers. Thus, an upwards directed force requires an anticlockwise directed torsion moment. If one wishes a forward directed movement of the protection body caused by a clockwise directed torsion moment, the inclination of the helix 1.272 must be reversed. More about that further on.

Now to the practical use. When the operator has filled the syringe 5 with the intended amount of medicine and controlled the content, the sterile packing of the needle material with the point protector in rest position is opened and the attachment to the syringe begun. At the screwing on of the needle body to the Luer lock part of the syringe the thumb/finger grip at the rear end of the protection body should contain, beside the torsion moment itself, an axially backwards directed force component.

When the screwing on, which from the front seen is done clockwise, is judged to be satisfactorily safe, the protection sleeve (not shown in the figures) is removed and usual testing of freedom from air inclusion is done. After that the puncture can be done, of course within beforehand sterile washed area, and after routine control aspiration the injection can be finished.

After performed puncture and control aspiration the point protector ought to be activated. This partly because the unprotected sharp needle point hardly may escape hurting the delicate inner vessel wall partly because a latter activation in practice cannot be done of the same operator at direct connection to the needle retraction. More about that later.

If protector activation is postponed until the injection is terminated it must wait until the operator has put on a suitable dressing over the operation area or got the patient's assistance to a temporary dressing. In both cases the syringe with its potentially contaminated puncture needle will probably be lying unprotected during the time.

Figure 12:
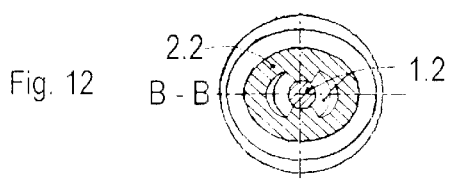

When the operator has his or her both hands available for the protector activation, it can be completed fast. First one widens the gap between the back side 2.23 of the protector and the fore side of the Luer lock part of the syringe so that the driver 2.27 reaches into the helical part of the grooves 1.272 at the outside of the anterior part of the needle body, see FIGS. 10 and 8. The gap widening is done by a light finger turning over and in the very gap. When the gap widening has released the surfaces 1.235/2.235 from their mutual engagement the protection body can be rotated clockwise in relation to syringe and needle so that the grooves 1.272 governs the drivers 2.7 up to the equatorial groove 1.22. See FIG. 13! It is somewhat deeper than 1.272 and can with the aid of form changing elasticity at the rear part of the protection body 2.2 fix the protector at its active position with the point enclosed in the protector tube 2.1 see FIG. 11 and FIG. 12! FIG. 12 shows the now oval shape of the protection body after the shape change of 1.22 compared with the circular form shown in FIG. 9. The protection body 2.2 is in fact designed so that its back part has an oval shape with unchanged inner circumference compared to FIG. 9. The minor axis of the oval initial shape is, in fact, a little shorter than in FIG. 12. The spring force for fixation in the groove 1.22 may be controlled partly by the choice of material partly by the choice of thickness of material. The choice of suitable elastic force is also important for the mounting of the needle protector at the needle and needle body. By compressing the oval protection body from the outside by a suitable tool it can be given the circular section that allows the drivers to pass over the groove 1.22 from behind without being caught and, via governing by the groves 1.271 with the same depth as 1.272 smooth via the grooves 1.272, be placed in its rest position. The outer compression in the plane of the major axis may cease, when the drivers 2.27 have reached into the foremost part of the grooves 1.272. The oval shape is suitably made elliptic owing to its simple design.

In this alternative a design has been used, where the activation movement of the protector is done by a rotation movement in opposite direction in relation to the screwing on of the needle. A prerequisite is that the fastening in the Luer lock screw is made safe enough so that the tightening at the Luer cone is not jeopardised at an activation rotation in opposite direction. This is especially important at early activation, i.e. before the injection.

However, nothing prevents that the same rotation direction for the activation as for the screwing on is chosen. This requires just that the helixes for the grooves 1.272 are changed from here illustrated right-hand spiral to the opposite.

It should also be pointed out that the number of groove helixes must not be limited to the here shown diametric pair. The thin dimension of the needle body may allow a triumvirate with the angle distance 120° or even double pair with the angle distance 90°. On the other side the advantages of an increased number are probably limited by the rotation asymmetry of the initial oval shape.

So far some examples of point protection for hypodermic needles according to the invention. Several alternative designs are of course possible within the framework of the invention idea.

Figure 16:
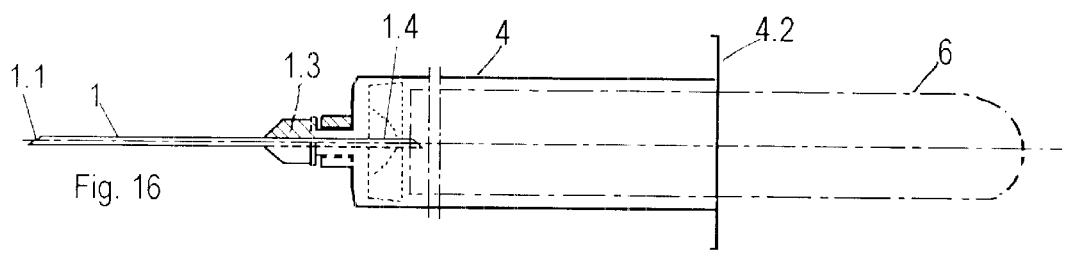
FIG. 16 shows the schematic construction of a puncture outfit for sampling according to the vacuum aspiration principle in existing design.
Figure 17:
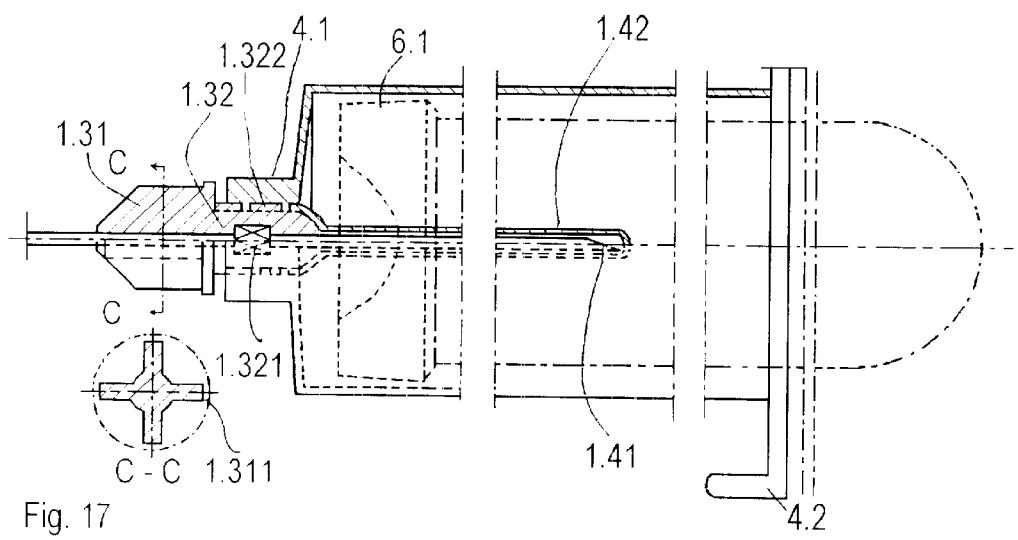
FIG. 17 shows details of FIG. 16 in larger scale.

Now over to another group of puncture needles namely the important number used for sampling. The initial method with aspiration to syringe has now mostly been abandoned, at least for venous sampling. It has now been replaced by vacuum aspiration, initially introduced under the trade mark VACUTAINER® (registered trade mark) but now supplied from several manufacturers. The device is shown schematically in the FIGS. 16 and 17.

The very puncture needle 1 is fixed to its needle body 1.3, the back threaded part 1.32 of which is screwed on the projecting muzzle of the transparent cylindrical holder 4.1. The screwing on is done with the aid of the attached protection sleeve (not shown in the figure) of the needle that fits to front part 1.31 of the needle body 1.3. The puncture needle 1 continues through the needle body, yet with interruption for a back flow protection 1.321, and is after that surrounded by a soft elastic bellows 1.42, which also encloses the backwards directed point 1.41 of the back end 1.4 of the needle 1 intended to puncture the bellows 1.42 and the elastic tightening stopper 6.1 of the test tube 6. The test tube 6 is evacuated to a suitable negative pressure.

The sampling is begun by that the test tube 6 is placed in the holder 4. After usual routine sterile wash of the patient's chosen skin area, one begins the sampling with a skin puncture and seeks with the needle point 1.1 the chosen blood vessel for a vessel access. The experienced operator then operates the test tube 6 so that the back point 1.4 of the puncture needle gets a transitory contact with the negative pressure of the test tube, through which a proper vessel wall passage is immediately shown by blood flow in the test tube 6, observable through the transparent wall of the test tube 6 and the holder 4. When the operator thus judges that he or she has established a safe situation for the needle point 1.1 the puncture of the test tube stopper 6.1 is completed so that full test tube flow is obtained. The operator can now change his or her hand grip so that the test tube can be drawn out when intended filling level has been reached. After that a new tube is put in until intended sampling is accomplished. The bellows 1.42 prevents efficiently all blood waste as well at the stopper 6.1 as within the holder 4. On the other hand the front point 1.1 of the puncture needle is of course potentially contaminated and must be detached from the holder 4 to be dispatched to a safe container for so called dangerous wastes. Unfortunately the experience shows many narrow escapes such as stab injuries at this procedure.

Figure 18:
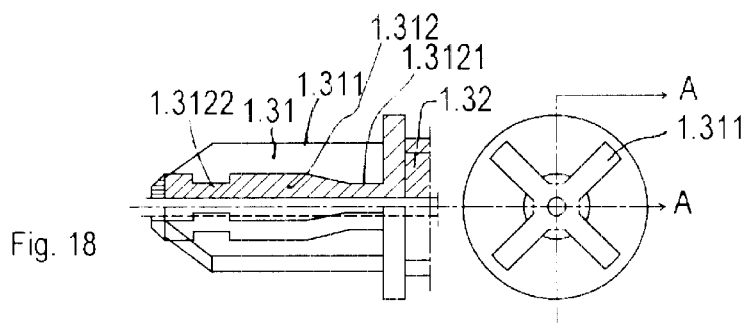
FIGS. 18 and 19 show an, in this invention, proposed design of the front part of the needle body.
Figure 19:
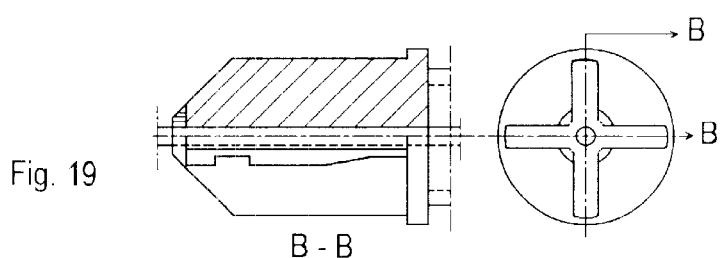

In the FIGS. 18, 19, 20, 21 and 22 a design of a point protector according to the invention is shown. The protection body's 2.2 four cylindrical sectors 2.24 straddle the front part 1.31 of the needle body 1.3 so that the four wings 1.311 of the needle body with a couple of tenth millimetre reach outside the outer surface of the protection body's cylindrical sectors 2.24 and by that provide grip possibility for the needle's 1 existing protection sleeve (not shown in the figures), which may, as before, be used for the attachment at the front muzzle 4.1 of the holder 4. The needle body's 1.3 cylindrical core 1.312 is now proposed to be designed with grooves 1.3121 and 1.3122 that fix the body 2.2 of the needle protector 2 with the aid of a holding border 2.24. The fixation in the anterior groove 1.3122 is final and corresponds to activated position of the point protector according to FIG. 22, while the fixation in the rear groove 1.3121 can be overcome by a moderate forward directed force at for instance the flanges 2.242 FIG. 21. Beside the external surfaces 2.243 may be grip-friendly designed. Around the back part an elastic O-ring or a suitably designed elastic cuff is attached, which produces a suitable contact force between the lock border's 2.241 inner surface and the core 1.312 of the needle body 1.3. The foremost part 2.21 of the protection body 2.2 is not slit. Instead it is a coherent disc-shaped bottom, which is a fastener for the thin walled tube 2, which forms the active point protector, and gives steadiness to the four cylindrical sectors 2.24. In FIG. 18, which shows the protector in rest position, one can see that the O-ring is partly balanced by the outer border of the wings 1.311. In the final stage of the activation movement forward the O-ring has rolled down, as shown in FIG. 20, and contributes now to the fixation in the groove 1.3122.

The activation movement may be mechanically coupled to the handling of the test tube 6. By elongating the rear part 1.4 of the puncture needle 1 one obtains a sufficient remaining movement distance for the test tube after the first trial contact between the negative pressure of the test tube and the needle 1.4. This distance, 6–7 mm, may be used and transferred to for instance the flange 2.242 as activation movement. In FIG. 23 a design alternative of such transfer is shown. Inside the holder tube 4 a movable basket 4.4, with weakly conical inner surface 4.41 adapted to the elastic stopper 6.1 of the test tube 6, is arranged. The basket 4.4 has, at its front part, an externally running groove 4.11 for engagement of three symmetrically arranged "claws" 4.52 outgoing from the back side of the driver 4.5. The claws 4.52 reach into the basket 4.4 through three narrow slits 4.02 in the wall of the holder tube. The axial length of the slits 4.02 determines the movement distance of the drivers 4.5. By that the movement distance of the basket 4.4 will also be limited. The movement distance shall correspond to the distance between rest position and protective position for the point protector 2. The external dimensions of the basket are chosen to give a moderate compressive stress against the inner walls of the holder tube. This entails that a suitable axial force is required for axial movement of the basket 4.4. In FIG. 23 the situation is shown with activated point protector and the filling of the actual test tube 6 just finished. When the operator begins the withdrawing of the test tube, the contact force between the outer surface of the test tube stopper and the inner surface of the basket should be sufficient to ensure that basket 4.4 and driver will follow so long as the slits 4.02 permit. When the test tube 6 comes loose from the basket 4.4, basket and driver 4.5 will stop at its rear limit position. When the next tube is inserted, the dimension relations between the basket position and the needle point 1.4 should be such that earlier mentioned trial puncture by the needle 1.4 can be done, before the test tube stopper dislodges basket 4.4 and driver 4.5. If the next tube 6 is intended for the fulfilling of a sampling succession in progress at the same patient, the test tube 6 may be pushed to the bottom for full drawing flow.

The automatic point protector activation means undoubtedly an important security gain, but the security has its price. A voluntary activation will, of course, be cheaper. It requires nor driver 4.5, basket 4.4, slits 4.02 or elongated tube puncture needle 1.4. Such a design is shown in FIG. 24. Probably one may, by colouring and grip friendly design, simplify the memorisation of this additional hand grip.

The designs of point protection for sampling material shown are just application examples of the inventive idea. Several other alternatives are possible without deviating from this notion. Some of these should be obvious for a man of the art.

Now the large number of equipment units intended for intravenous access remain. FIG. 25 shows a usual design and FIG. 26 shows in large magnification a schematic picture of the central and rear part of the cannula body 3.2.

The puncture needle 1 has its point region free over the bevel cut with the sharp point 1.1 and some millimetre of its cylindrical part. After that the needle is surrounded by the cannula 3 to its entire anterior part right to the central cylindrical chamber 3.20 of the cannula body 3.2. The cannula type shown in the figure has an upper port 3.21 that from above opens out into the cannula chamber 3.20. The connection is provided with a non return barrier 3.201 designed as a soft cylindrical thin walled tube that with some compressive stress is in close contact with the inner surface of the cannula chamber. By that the tightening against back flow becomes very efficient. In fact the stopper 3.211 does not really need to exercise any tightening function. This is under the assumption that the barrier is not subjected to any tampering with, for instance from the inside the chamber 3.20. This chamber opens out and widens backwards to its rear entry 3.22. The conicity corresponds with accepted standard 6%. Also its length follows applicable standard so that coupling details for such connections, first hand a stopper 3.23 can be used, which is needed when the puncture is accomplished awaiting actual infusion. Until the puncture is accomplished the port 3.22 is occupied by the anterior conical part 1.21 of the needle body 1.2, which by the way does not either fill any tightening task, but is important for stabilising the unit: needle+cannula 3+cannula body 3.2, during the puncture procedure. This is really a precision demanding task. Play in the equipment cannot be allowed. The conical front part 1.21 of the needle body 1.2 is therefore often designed as a six-pointed star, seen in section, see FIG. 33! The needle 1 continues after the conical front part 1.21 of the needle body backwards to a signal chamber 1.20 with transparent walls to show accomplished and desired contact with the blood flow.

The point protection has to be adapted to the conditions here described. The needle 1 will be withdrawn just after an accomplished puncture. The movement of the point protector may be mechanically coupled to the needle retraction. If possible this should happen without additive demands of voluntary efforts from the operator's side. The procedure itself is sufficiently demanding. The movement itself in relation to the needle 1 to active position requires that the protector be kept still in relation to the cannula 3 and cannula body 3.2 until its protective position has been reached. Then the fixation to the cannula 3 and cannula body 3.2 has to cease and be replaced by a safe fixation to the needle point region. The fixation arrangement itself may be located to another part of the needle. The location must, of course, be chosen such that the puncture is not made more difficult.

A nearby alternative is shown in FIG. 27. The holding of the protector 2 is obtained by the position of its thin walled tube between the needle 1 and the cannula 3 so that in rest position it is entirely covered by the cannula 3 and gets its front end 2.1 ~1–2 needle diameters behind the cannula's 3 front end 3.1. When the cannula 3 with stationary needle 1 is advanced into the punctured vein, the point protector part under the cannula tube 3 will accompany it sliding along the needle 1, until the back edge of the point protector 2.2 is caught by the groove 1.212 in the driver 1.210 fastened at the needle body's 1.2 front part 1.21, and irreversibly fixed there. If it should ever happen that the cannula movement is not sufficient for reaching the fixation in protective position, the next operation, retraction of the needle with stationary cannula 3, will complete the movement to fixation position in the groove 1.212. The distance between back edge 2.2 and the groove 1.212 is adjusted to the activation distance for the protector 2. The situation for the needle point is shown in FIG. 3 and FIG. 29. The driver has at its front edge 1.21 an outer circular groove 1.214 to lodge an elastic O-ring, which assists the inherent elasticity of the driver tube 1.210 to safeguard the fixation of the edge 2.2 in the groove 1.212. The sleeve 1.210 should be slit 1.215 into two identical halves to one half its length to bring about a more comfortable extension, when the edge 2.2 passes the conical part 1.213 of the sleeve 1.21. As a cheaper and often better alternative to an O-ring may a suitable designed rubber stocking be used.

FIG. 28 shows an alternative design of the driver 1.21 as weakly conical but still with a frontal slotting into two halves, the inherent elasticity of which is thought to be sufficient for fixation in protective position. Thus, here no O-ring is required. Of course it is essential that the withholding force from the inner surface of the cannula 3 is sufficient.

FIG. 29 shows the situation just when the protector has reached its activated position. Continued needle retraction implies that the needle is set free from the cannula body, with its needle point rendered harmless, and dispatched to a safe container for dangerous wastes.

The practical consequences of designs according to the FIGS. 27 and 28 are judged to affect just slightly the puncture procedure itself. It is true that the accommodation of the thin walled tube 2 under the cannula 3 leads to an inevitable increase of the outer diameter of the cannula 3. With suitable design of the contact surfaces it may involve a decreased risk for wrinkling of the cannula point at skin and vessel wall penetration. At unchanged wall thickness of the cannula and unchanged outer diameter of the needle the diameter increase will stop at 0,20–0,30 mm, if plastic material is used. For the alternative, stainless steel, a wall thickness of about 0,05 mm should be enough. This would cause a diameter increase of about 0,10 mm, but the cost increase will probably be noticeable. In relation to the gain in decreased stab injury frequency the diameter increase should be tolerable.

In order entirely to avoid touching puncture active parts of the needle 1 and cannula 3 including cannula body 3.2, the whole protective arrangement at rest position must be located as a whole in the cannula body chamber 3.20, possibly with temporary contribution from the cannula tube 3 itself. This restriction brings design complications but allows all the same several other alternatives.

In FIG. 30 such an example is shown. The thin walled tube-shaped protector 2 is at its front edge provided with an internal thickening and is frontally slotted into two halves. In rest position they are prevented from closing until the needle point 1.1 has passed and by that left the muzzle part 2.1 of the tube 2.0 internally empty. Before that the thickened front part 2.1 rides on the outer surface of the needle and holds the outside of the front part 2.1 pressed against the inside of a fixation sleeve 2.3, which with its anterior conical part strains against the inner side of the cannula's back end just in front of the opening out into the cannula body's 3.2 chamber 3.20. The bearing pressure is adjusted with the aid of dimensioning and choice of surface structure such that the detainment continues, when the needle 1 is retracted. During the early detainment the protectors front part 2.1 straddles the needle 1 as in section A—A in FIG. 30, but resumes its circular section as in section B—B FIG. 31 by that letting loose the coupling to fixation sleeve 2.3 and allowing said sleeve to get dislodged by the pulling force of the stocking 3.61, the back end of which is fastened at the protector's body 2.2. When the protector has reached its active position another stocking 1.6, the end of which is fastened to the needle body 1.2 and shown folded up in FIG. 30, will drag the entire protector along. Simultaneously the fixation sleeve 2.3, which now has got dislodged from the cannula 3.0, is dragged along. Just the length of the back entry 3.22 of the cannula body is now remaining before the needle 1 is entirely freed from the cannula 3 and may, with its point adequately rendered harmless, be dispatched to its safe storage place in the waste container.

The possibilities of getting a holdback function for a protector with its rest position within the cylindrical chamber 3.20 of the cannula body 3.2 are limited by the fact that the delicate back flow protector 3.301 leaves free just a limited part of the cylindrical chamber wall. For a temporary holdback just a couple of millimetres remain before the Luer conic entry 3.22 begins.

In FIG. 32 is shown a proposed arrangement 7 in the shape of a left-conical circular disc 7.1 carried by a cylindrical hub 7.2, which also contains a folded-up, thin, air pervious stocking 1.6 with its back end fastened at the needle body 1.2. Thickness, material, shape and tensile properties of the disc 7.1 are adjusted so that the fixation arrangement can sustain moderate forces and keep back the point protector arrangement inside, when the needle 1.0 is retracted, but will yield and follow continued needle retraction, when the stocking 1.6 is completely drawn out, which is adjusted to happen, when the protector 2 has reached active protective position at the needle 1.0.

With unchanged dimensions for the cannula body 3.2 and unchanged design of the needle body 1.2 the available space for the stocking 1.6 in FIG. 30 and for stocking+disc 7 in FIG. 32 will be scarcely sufficient for most products.

A nearby step is to elongate the cylindrical part of the cannula chamber 3.20 with 4 to 5 mm with otherwise completely unchanged design. By that no other complication is caused than an elongation the needle 1.0 with the same length.

Another possibility is a changed design of the needle body. Its conic part that fits to the rear conical entry 3.22 of the cannula body does not fill any need for liquid tightening. Its task is just to give a stabile coupling between the needle and cannula bodies. Thus, its length may be decreased with at least 4 mm, without embarrassing loss of stability, under the assumption that the blunt star-shaped section of FIG. 33 is preserved.

As for this it should be noted that a syringe handle integrated with the needle body as in the Swedish patent 9303325-6 and PCT/SE94/00951 will with good measure compensate for the loss of rigidity and stability that this proposed shortening of the front end of the needle body 1.21 is causing. This essential ergonomic gain regarding precision at puncture operations will probably before long be commonly demanded, especially as demands of procedure simplification probably is in the time. By that a general future overhaul of the construction of the needle body will be motivated, especially as the integrated handle makes the shield of the needle body unnecessary.

A third possibility of space addition to the cannula body's chamber 3.20 is shown in FIG. 34, namely an adapter 8, the front part of which fits to the rear opening of the cannula body with its tapering sleeve-shaped part 8.11, and the outer part 8.12 of which accurately connects to cannula body's outer surface inclusive its external Luer lock outgrowth 2.28 to secure turning stability. The rear part of the adapter is a copy of the cannula body with, inter alia, the same Luer lock outgrowth 8.8 for turning stability safeguarding and inside adaptation of the tapering sleeve-shaped part 8.11 to the needle body's conic part 1.21.

Figure 40:
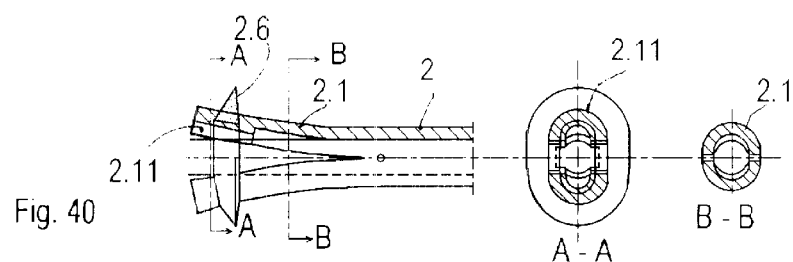

With the aid of the arrangement 7 the point protector may be simplified compared with the FIGS. 30 and 31. In FIG. 40 such a simplification is shown. The thickened front end 2.11 of the point protector 2 extends the tube halves 2.1 over the needle tube 2.0. The inherent elasticity of the halves is helped by an elastic O-ring 2.6 to close the gap. This O-ring has in the figure been given a triangular section (gives increased positional stability) but other section shapes, and earlier mentioned rubber stocking, may be used. The essential is an adjusted force to close the gap, when the needle point has passed, i.e. the same function as wanted in the FIGS. 30 and 31. As in the designs of FIGS. 30 and 31 the thickened front part has to resist moderate backwards directed forces without that the needle point penetrates the swelling. The rear end of the protector tube 2.0 or possibly the protection body 2.2 shall be fixed to the arrangement 7 and be retracted via the stocking 1.6, when the protector has reached its activated position at the needle. By that needle 1 and fixation arrangement may, in rendered harmless shape, be finally parted from cannula 3 and cannula body 3.2 and dispatched to a protective container for dangerous wastes.

It should be added that a safe function of the point protector of FIG. 30 and FIG. 31 assumes that the reciprocal orientation of the point protector's splitting plane and the needle point 1.1 corresponds to the figure, i.e. that the radial symmetry plane of the point does not substantially deviate from a 90-degree angle at the delivery and that the needle body at the use is not turned more than ±60° maximum. Larger turning of the needle body in relation to the protector 2 will bring about risk to place the needle point dangerously close to the splitting plane at active position with risk for penetration of the protective barrier 2.11.

Figure 41:
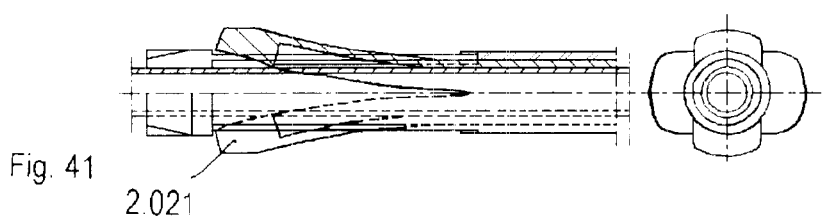
Figure 42:
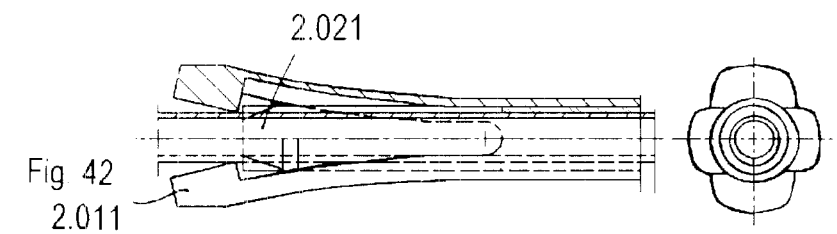
Figure 43:
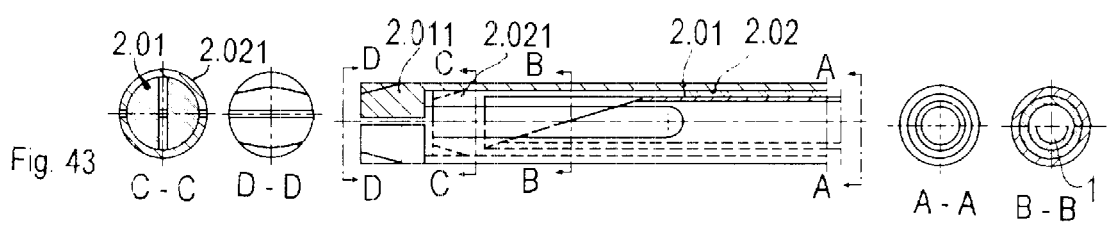

A way to avoid this risk is shown in the FIGS. 40, 41, 42, and 43. This point protector is built up of two concentric thin walled tubes 2.01 and 2.02. At their anterior parts they are split in mutually identical halves along a length adjusted for a balanced spring return to their cylindrical start shape. The two tubes 2.01 and 2.02 are further provided with half circular bottoms, the axially running parting lines of which form 90° with each other. The mantle of the outer tube 2.01 lacks a 30° wide strip at each side of the cleaved halves yet with exception for the neighbourhood of the unchanged half circular bottom, while the mantle of the inner tube is half circular along its entire split length. See FIG. 43 section C—C and section D—D. FIG. 41 shows the protector seen from the side at rest position, while the FIG. 42 shows the protector 2 seen from above. FIG. 43 shows the protector just arrived at activated position. The cut away strips 4×30° are meant to decrease the force needed for separating the bottom halves 2.021 so that they straddle the needle 2 at the protector's rest position.

So far described arrangements give an instantaneous fixation of the muzzle part of the protector 2.1, when a determined retraction limit has been passed. If one instead permits a few millimetres drawing back for the impact of the fixation, the arrangement may be simplified. See FIG. 35 and 36!

Here the muzzle part 2.1 consists of an inner tube-formed part 2.11 with moderate coefficient of elasticity and good elasticity and an outer more rigid enclosing part 2.13 that connects to the protector tube 2. The foremost half 2.111 of 2.11 is fixed to 2.13, while the back half 2.112 is just in close contact with 2.13. When the protector is not activated the needle 1 is tightly enclosed by the part 2.11. Simultaneously the part 2.112 is extended so much that its material is close to its yield point. When the needle point has been retracted past the rear border of the part 2.112 the extension ceases and the part 2.112 returns to a rest position in conic form. It does no longer permit an in relation to the protector forward directed needle movement beside what is needed for a braking impact.

This described back movement barrier may be designed in several different ways by using elastic relaxation. It is desirable that the whole unit 2.1 should be possible to make in one piece but the requirements for elasticity of the part 2.112 may conflict with the need for rigidity of the part 2.13. A reversible extension of 20 to 30% or more will probably be needed for the part 2.112 but suitable material for 2.13 usually permits just 10% maximum.

Some examples of suitable designs for the part 2.11 are shown in the FIGS. 35 to 39. The foremost part 2.111 is made cylindrical with comparatively coarse material thickness. The rear part 2.112 is made conical with thinner material.

Alternatively a design in poly propylene for the entire detail 2.1 may be possible if the part 2.112 is made as a frustum of a cone with longitudinal against the border to 2.111 pointed slotting. The detail 2.1 may also be made as an, at a start, cylindrical tube, the rear part 2.112 of which is made longitudinally wave shaped, against the rear end with growing amplitude corrugated so that the wave tops may be housed within a suitable circumscribing conic form, remaindering of some old lampshades. By that the elastic strain will be limited when the part 2.13 is to enclose the puncture needle. In the slit alternative the form change to cone may, of course, be eased by a thin fixed film of a suitable elastic material.

Still another design alternative is shown in FIG. 44 that shows the protector 2 close to its activated protective position at the needle 1.0. Here the fixation occurs with the aid of a circumscribing, not perforating groove at the surface of the needle. The groove 1.9 has to be clearly defined and placed in adjusted nearness to the needle point 1.1 but at sufficient distance from there not to interfere with the foremost tapering and tight-fitting point of the cannula tube 3.0. This to avoid hampering the advancement of the cannula. The simplest way of shaping the groove 1.9 is to let the needle 1.0 be made as two thin walled concentric tubes one outer 1.5 and one inner 1.6. As the depth of the groove will be limited, probably 0.10 mm maximum, an accurate identification of groove borders is necessary for a secure fixation. The protector's contact with the groove 1.9 is effected by an essentially circularly running part of the protector's rear and into four quadrants divided part 2.2 surrounded by a comparatively strong elastic O-ring 2.6 Intended to reinforce the inherent elastic, centripetally directed pressure from the four quadrants. The surface 2.21 of the protector 2, intended to be situated in the groove 1.9 at activated position, is designed so that the pressure is concentrated to the groove borders. Thus, the shape may be compared with the inner surface of the outer ring in a spherical roller bearing. A homogeneous material in the entire protector 2 is of course desirable. The material has to satisfy demands of a sufficient flow limit and modul of elasticity. An acetal polymer may be a suitable choice. The fixation at active position is designed to resist a forward directed dislodging force. Thus, the need for the stocking 1.6 disappears and the holdback disc 7 becomes simplified a little, compared with FIG. 32.

In the FIG. 44 the inner tube 1.6 has schematically been shown as extremely thin compared with the outer one 1.5. In reality one should use practical testing to determine what wall thickness is required to preserve sufficient bending resistance. Even for extremely small-bore cannulae for instance 0,8 mm may the space permit sufficient wall thickness, as even an inner diameter of 0,2 mm should suffice for fast flow of sufficient blood volume to the signal chamber 1.20 in FIG. 25. As mentioned earlier it may sometimes be desirable that the groove 1.9 at the start is closed to avoid shelf deformation of the cannula's 3 over the groove situated part. Shelf deformation might cause wrinkling risk, when the cannula after a completed vessel puncture is advanced over the needle point to desired intravasal position. Closing may be effected by making the rear part of the outer tube of the needle 1.5 displaceable backwards so that the groove is automatically opened at a suitable stage of the protector activation, for instance when the needle begins its retraction movement out of the stationary cannula. The mobility of the rear part of the outer tube 15 should, for stability reasons, be limited to the groove width only in axial direction and not permit rotation movement in relation to the needle.

Also, the designs shown in this part are just examples chosen among several possible designs within the framework of the invention.

Sometimes so called butterfly needles are used for temporary, peripheral intravenous accesses as well for ambulatory requirements as for hospital treatment, especially for difficult of access or otherwise arduous situations, for instance for scalp veins within the paediatric and for crural phlebography within the roentgen diagnostic. Here the point protector has an important positive effect, beside the protection against infection, consisting in protection of the endothelium of the punctured vessel, when the access is established.

FIG. 46 shows an existing common design of a butterfly needle with belonging catheter tube 3 and terminating standard coupling for connection to a syringe or infusion unit.

In FIG. 47 the proposed completing with a point protector according to the invention is shown. The needle body's 1.2 wings 1.25 are partly covered by the protector body's 2.2 wings 2.25, which are loosely connected with the wings 1.25 by a collar stud-shaped outgrowth 1.27 and an aperture 2.26 that limit the mutual mobility between needle body and protector body mainly to a defined distance in the direction of the needle axis—the activation length. The ends 2.261 respectively 2.262 of the slits 2.26 is designed for a fixation of the "collar stud" 1.27 in the end positions. This fixation is made irreversible in the foremost position 2.61, inter alia, by a special design of the neck of the collar stud, and detachable in the rear position 2.62. The displacement can be done by a thumb/forefinger grip over the front respectively back borders of the wings. The mutual shaping of respective pair of wings is adjusted for such a displacement from rest position to activation position. Besides the rear end 2.262 of the slit 2.26 permits the mutual movement in transverse direction that arises, when the operator is turning up the wings for a firm thumb/forefinger grip before the very puncture. When the blood vessel contact has been established, the needle is hold still, while the wings are turned down so that the protector can be moved to its activated position as in FIG. 24 and fixated there. The mutual displacement of the protector body 2.2 in relation to the needle body 1.2 is guided, beside by the collar studs 1.27 and the slits 2.26, by suitably shaped guide ridges 1.28 and 2.28. In the active position the point is enclosed in its protector both in its intravasal situation and after the drawing out and displacement to a safe waste container.

In the end the problem should be considered, which is mentioned at page 2, to prevent touching of the potentially contaminated outer surfaces of the needle point protector. As mentioned this desideratum is fulfilled by the alternatives of mechanical point protector arrangements for the puncture needles for blood vessel access described at the pages 12 to 19. For these it is true that the puncture active outer surfaces and by that potentially contagious outer surfaces are protected by surrounding "clean" surfaces, when the puncture needle is withdrawn from the patient's tissues to be dispatched to its protected container for dangerous wastes.

For other needle categories, where the needle has a liquid transporting function and one, to protect the inner wall of the vessel from contact with the sharp needle point, strives to attain an activated position of the point protector, when the needle has reached a satisfying intravasal position is, of course, the front part of the point protector potentially contagious.

In FIGS. 49 and 50 a simple arrangement is shown by which potentially contagious parts of the point protector in a safe way are covered by an elastic tight stocking 2.8 being unrolled forward to cover the tube part 2.0 of the point protector, while a suitably shaped O-ring prevents the protective stocking from sliding back over the protector 2.0.

FIG. 49 shows the situation when the needle 1, with its activated point protector 2, has just been disengaged from the patient. The elastic stocking 2.8 is to for the most part rolled up over a suitably shaped O-ring 2.89 to a torus-shaped body surrounded by the driver 2.84 built up of a rear part 2.842 and a front part 2.841. The latter have the task of preventing too early unrolling. The very hindmost part of the stocking 2.8 is unrolled and is covered by the rear part 2.842 of the driver 2.84 and fixed to the point-protector 2. The task of the driver is now to unroll the stocking as fast as possible. In contrast to the activation of the very point protector the unrolling is more difficult to automate mechanically. Nevertheless, even a voluntary operation may with satisfying safety be connected to a routine part operation if the connection seems natural and personally important.

Here the unrolling is ended by that the whole driver is taken charge of as waste. It may then be natural for the operator to begin the unrolling after that she or he has temporarily fastened required tape material at the driver that she or he holds with the compressing hand, after which the soon free other hand applies the dressing over the puncture spot.

Concerning the design of the stocking 2.8 note that its inner diameter should be smaller than the outer diameter of the point protector so that a suitable contact pressure is attained against the outer surface of the protector is attained. By that as well the unrolling as the safeguarding in an unrolled situation as in FIG. 50 is eased.

As for this it can be said that this principle with an unrolling protector may sometimes be used even for the mechanical protector function. Here the protective stocking should, of course, be reinforced by a suitable fibre material, for instance Aramid® (reg. trade mark) in a weaving technique that allows necessary extension in the torus form and enough reinforcement closeness in unrolled state over the point region. To neutralise the injury risk from the very needle point a suitably shaped O-ring, probably with rectangular or triangular section should give for normal loads acceptable protection.

So far decontamination methods by covering. A different method is shown in FIGS. 51 to 54. Here the principle is a retraction combined with turning inside out of the potentially contagious surface. The retraction is effected by relaxation of an, at the start, to maximum elastic extension, ~500%, extended tube or stocking 2.7 that at the relaxation tries to get back to essentially original unloaded length and forced to a turning inside out so that the originally outwards turned and potentially contagious surface now will be turned inwards and by that protected from touching.

Figure 51:
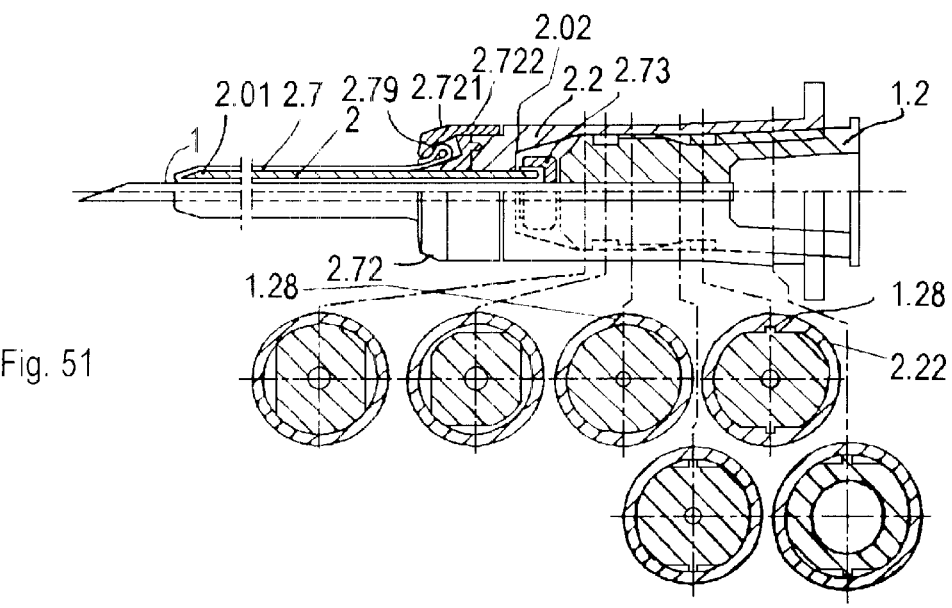
Figure 52:
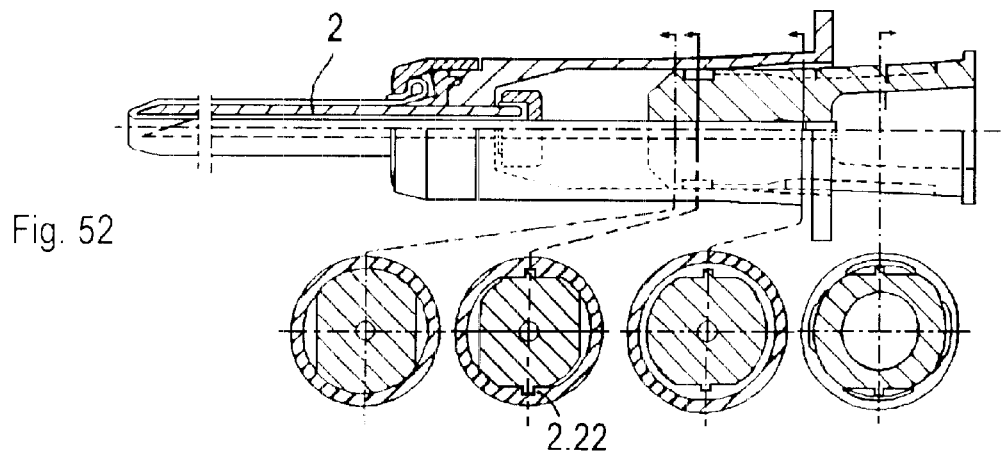
Figure 53:
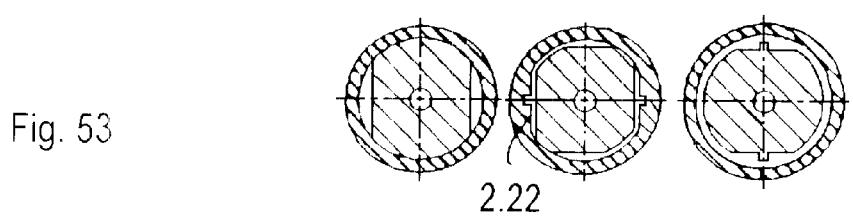
Figure 54:
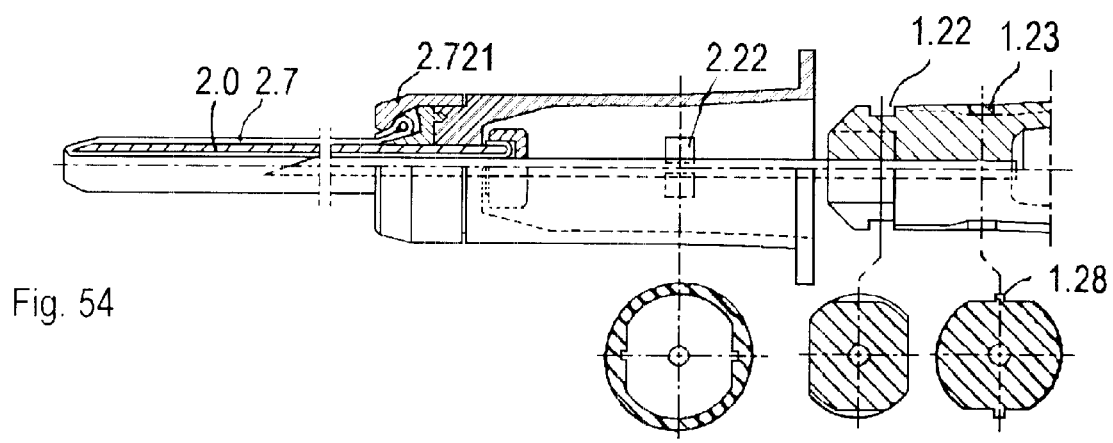

FIG. 51 shows the situation, when the point protector is in rest position and the needle is ready for the puncture. The elastic tube or stocking 2.7 extended to a length, 5× times the relaxed length, and fixed to an external fixation arrangement 2.72, runs from there externally forward to be turned inside out over the front end 2.01 of the protector tube 2 and continues backwards internally between the protector 2 and the needle 1 away to the rear border 2.02 of the protector where it is turned and fixed to the disc 2.73. The needle body 1.2 and the protector body 2.2 cooperate in principle as in the FIGS. 6 and 7 in rest position and by movement to activated position but with the difference that rotation movement with relation to each other is prevented by two diametrically arranged ridges 1.28 running from the back border of the needle body's activation position past the needle body's rest position recess 1.234 right to the protector body's back border at rest position (FIG. 51). Beside that the stop positions for rest and activation positions are adjusted for this unchanged turning position in relation to the needle body. In the active position according to FIG. 54 a 90-degree turning anticlockwise is permitted but not before a moderate voluntary turning moment according to the sections in FIG. 52. These sections show that the protector body now can be advanced further forward in relation to the needle body so that the situation looks as in FIG. 54. If one now by a thumb/forefinger grip advances the front fixation arrangement 2.721 of the stocking 2.7 the turning of the rear end of the stocking 2.7 around the O-ring 2.72 will obviously get loose and the freed parts of the stocking strive to regain its unloaded length, i.e. ⅕ of the unrelaxed length. By advancing the protector with its protector body still further one can now effect that desired part of the protective stocking 2.7 becomes retracted in turned inside out state inside the protector tube 2.0. In FIG. 54 the arrangement the arrangement of the smoothing down of the needle body's front part from the activation position with the shoulders 2.22 in the groove 1.22 that after the described 90-degree turning permits the advancement of the protector and protector body. This could possibly imply risk that the entire needle could leave the protector if the needle would not be gradually getting squeezed more firmly by the rear part of the stocking 2.8 that expands in radial direction as the forward directed pulling force decreases. The tolerances needle/stocking/protective tube must, of course, be accurately adjusted at the beginning.

What is claimed is:

1. A puncture needle assembly for preventing blood infections during hypodermic puncture procedures, comprising:
    a hollow hypodermic needle having a sharp end and a hollow interior channel;
    a point protector comprising a thin walled tube movable from an inactive position behind the sharp end such that the sharp end of the needle is exposed from the tube, to a protective position ahead of the sharp end such that the tube is protectively disposed around the sharp end for preventing accidental injurious contact with the sharp end, wherein the needle is received within the tube and the point protector is configured for facilitating movement of the tube from the inactive position to the protective position and for hindering movement of the tube out of the protective position, the point protector having a distal end disposed towards the sharp end of the needle, and the distal end being sufficiently blunt to resist penetration of human tissue in the protective position, wherein the tube is configured and dimensioned to have a sufficient length for entering the patient along with the needle prior to positioning the tube in the protective position such that the tube can be placed in the active position when disposed inside the patient;
    an engageable member operatively associated with the point protector for moving the protector to the protective position, the engageable member being configured and disposed for operable engagement by another object that is movable relative to the needle for causing the engageable member to move the point protector without relying on an association with a portion of the patient; and
    a body portion supporting the needle and configured for mounting to a parenteral fluid vessel with the needle in fluid communication therewith.

2. The puncture needle assembly of claim 1, wherein the point protector is configured for substantially preventing movement of the tube away from the protective position.

3. The puncture needle assembly of claim 2, wherein the point protector comprises a locking mechanism configured for locking the tube in the protective position, wherein the locking mechanism is configured and disposed to impede manual unlocking thereof.

4. The puncture needle assembly of claim 1, wherein the engageable member is disposed such that the point protector is operable to move the tube from the inactive position to the protective position while held by a user at a safe distance behind the sharp end of the needle.

5. The puncture needle assembly of claim 1, wherein the engageable member is operatively engageable with a functional member for automatically moving the tube from the inactive position to the protective position upon movement of the functional member in relation to the needle, wherein the functional member comprises one of an aspiration tube, a cannula, a syringe, and a plunger.

6. The puncture needle assembly of claim 1, wherein the engageable member comprises a manipulable portion configured for moving the tube from the inactive position to the protective position.

7. A puncture needle assembly for preventing blood infections during hypodermic puncture procedures, comprising:
    a hypodermic needle having a sharp end;
    a point protector comprising a thin walled tube movable from an inactive position behind the sharp end such that the sharp end of the needle is exposed from the tube, to a protective position ahead of the sharp end such that the tube is protectively associated with the sharp end for preventing accidental injurious contact with the sharp end, wherein the point protector is configured for facilitating movement of the tube from the inactive position to the protective position and for hindering movement of the tube out of the protective position, the point protector having a distal end disposed towards the sharp end of the needle, and the distal end being sufficiently blunt to resist penetration of human tissue in the protective position; and
    an engageable member operatively associated with the point protector for moving the protector to the protective position, the engageable member being configured and disposed for operable engagement by another object that is movable relative to the needle for causing the engageable member to move the point protector without relying on engagement with a portion of the patient to move the point protector, wherein the engageable member comprises a manipulable portion that is rotatable for moving the tube from the inactive position to the protective position.

8. The puncture needle assembly of claim 7, wherein the manipulable portion is rotatable substantially coaxially with the needle for moving the tube from the inactive position to the protective position.

9. The puncture needle assembly of claim 6, wherein the point protector comprises a second portion, wherein one of the manipulable portion and the second portion comprising a groove have a groove depth and a recess of a recess depth greater than the groove depth, and the other of the manually operable portion and the second portion comprising a protrusion movably received in the groove, the recess being configured for trapping the protrusion therein in the protective position.

10. A puncture needle assembly for preventing blood infections during hypodermic puncture procedures, comprising:
   a hollow hypodermic needle having a sharp end and a hollow interior channel;
   a point protector comprising a thin walled tube movable from an inactive position behind the sharp end such that the sharp end of the needle is exposed from the tube, to a protective position ahead of the sharp end such that the tube is protectively disposed around the sharp end for preventing accidental injurious contact with the sharp end, wherein the needle is received within the tube and the point protector is configured for facilitating movement of the tube from the inactive position to the protective position and for hindering movement of the tube out of the protective position, the point protector having a distal end disposed towards the sharp end of the needle, and the distal end being sufficiently blunt to resist penetration of human tissue in the protective position; and
   an engageable member operatively associated with the point protector for moving the protector to the protective position, the engageable member being configured and disposed for operable engagement by another object that is movable relative to the needle for causing the engageable member to move the point protector without relying on an association with a portion of the patient wherein the engageable member comprises a manipulable portion configured for moving the tube from the inactive position to the protective position, and the manipulable portion is configured for extending adjacent wings of a butterfly needle, such that relative movement between the manipulable portion and the wings causes the movement of the tube from the inactive position to the protective position.

11. A puncture needle assembly for preventing blood infections during hypodermic puncture procedures, comprising:
   a needle having a sharp end;
   a point protector comprising a thin walled tube movable from an inactive position behind the sharp end such that the sharp end of the needle is exposed from the tube, to a protective position ahead of the sharp end such that the tube is protectively associated with the sharp end for preventing accidental injurious contact with the sharp end, wherein the point protector is configured for facilitating movement of the tube from the inactive position to the protective position and for hindering movement of the tube out of the protective position, the point protector having a distal end disposed towards the sharp end of the needle, and the distal end being sufficiently blunt to resist penetration of human tissue in the protective position; and
   an engageable member operatively associated with the point protector for moving the protector to the protective position, the engageable member being configured and disposed for operable engagement by another object that is movable relative to the needle for causing the engageable member to move the point protector;
   wherein the tube comprises a flexible sheath fitted around the needle and folded back over itself in the inactive position.

12. The puncture needle assembly of claim 11, wherein the flexible sheath is rolled up about itself in the inactive position.

13. The puncture needle assembly of claim 12, wherein the engageable member comprises an unrolling portion disposed about the rolled-up tube and associated therewith for unrolling the tube to the protective position.

14. A puncture needle assembly for preventing blood infections during hypodermic puncture procedures, comprising:
   a hypodermic needle having a sharp end;
   a point protector comprising a thin walled tube movable from an inactive position behind the sharp end such that the sharp end of the needle is exposed from the tube, to a protective position ahead of the sharp end such that the tube is protectively associated with the sharp end for preventing accidental injurious contact with the sharp end, wherein the point protector is configured for facilitating movement of the tube from the inactive position to the protective position and for hindering movement of the tube out of the protective position, the point protector having a distal end disposed towards the sharp end of the needle, and the distal end being sufficiently blunt to resist penetration of human tissue in the protective position; and
   an engageable member operatively associated with the point protector for moving the protector to the protective position, the engageable member being configured and disposed for operable engagement by another object that is movable relative to the needle for causing the engageable member to move the point protector;
   wherein the tube comprises an end portion having at least first and second end parts separated by a substantially longitudinal slot, the end parts being held apart by the needle disposed therebetween in the inactive position, and the end parts being biased to move towards each other upon withdrawal of the needle from between the end parts for substantially closing around the needle and preventing passage of the needle therebetween in the protective position.

15. The puncture needle assembly of claim 14, wherein the tube comprises coaxial first and second tubes each having a said end portion, wherein the slot separating the first and second slots of the first tube is disposed approximately normal to each other.

16. The puncture needle assembly of claim 1, wherein the sharp end of the needle is offset from the channel.

17. The puncture needle assembly of claim 11, wherein the needle comprises a hollow hypodermic needle.

18. A puncture needle assembly for preventing blood infections during hypodermic puncture procedures, comprising:
   a hollow hypodermic needle having a sharp end; and
   a point protector comprising a thin walled tube having an inactive position behind the sharp end such that the sharp end of the needle is exposed from the tube, and a protective position ahead of the sharp end such that the tube is protectively disposed around the sharp end for preventing accidental injurious contact with the sharp end;

wherein the needle is received within the tube;

wherein the point protector is configured for facilitating movement of the tube from the inactive position to the protective position and for hindering movement of the tube out of the protective position; and a body portion supporting the needle and configured for mounting to a parenteral fluid vessel with the needle in fluid communication therewith;

wherein the point protector comprises an engageable member operatively associable with a functional member for automatically moving the tube from the inactive position to the protective position upon movement of the functional member in relation to the needle, the functional member being configured to perform hypodermic procedure function.

19. A puncture needle assembly for preventing blood infections during hypodermic puncture procedures, comprising:

a hollow hypodermic needle having a sharp end; and a point protector comprising a thin walled tube having an inactive position behind the sharp end such that the sharp end of the needle is exposed from the tube, and a protective position ahead of the sharp end such that the tube is protectively disposed around the sharp end for preventing accidental injurious contact with the sharp end;

wherein the needle is received within the tube;

wherein the point protector is configured for facilitating movement of the tube from the inactive position to the protective position and for hindering movement of the tube out of the protective position; and wherein the point protector comprises an engageable member operatively associable with a functional member for automatically moving the tube from the inactive position to the protective position upon movement of the functional member in relation to the needle, the functional member being configured to perform hypodermic procedure function; and wherein the functional member comprises an attachment, and the point protector is operatively associable with the functional member for automatically moving the tube from the inactive position to the protective position separation of the attachment from the point protector.

20. The puncture needle assembly of claim 18, wherein the functional member comprises a syringe plunger.

21. A puncture needle assembly for preventing blood infections during hypodermic puncture procedures, comprising:

a hollow hypodermic needle having a sharp end; and a point protector comprising a thin walled tube having an inactive position behind the sharp end such that the sharp end of the needle is exposed from the tube, and a protective position ahead of the sharp end such that the tube is protectively disposed around the sharp end for preventing accidental injurious contact with the sharp end;

wherein the needle is received within the tube;

wherein the point protector is configured for facilitating movement of the tube from the inactive position to the protective position and for hindering movement of the tube out of the protective position;

wherein the point protector comprises an engageable member operatively associable with a functional member for automatically moving the tube from the inactive position to the protective position upon movement of the functional member in relation to the needle, the functional member being configured to perform hypodermic procedure function; and wherein the point protector is frictionally engageable with the functional member for the automatic moving of the tube with respect to the needle from the inactive position to the protective position.

22. A puncture needle assembly for preventing blood infections during hypodermic puncture procedures, comprising:

a hollow hypodermic needle having a sharp end; and a point protector comprising a thin walled tube having an inactive position behind the sharp end such that the sharp end of the needle is exposed from the tube, and a protective position ahead of the sharp end such that the tube is protectively disposed around the sharp end for preventing accidental injurious contact with the sharp end;

wherein the needle is received within the tube;

wherein the point protector is configured for facilitating movement of the tube from the inactive position to the protective position and for hindering movement of the tube out of the protective position;

wherein the point protector comprises an engageable member operatively associable with a functional member for automatically moving the tube from the inactive position to the protective position upon movement of the functional member in relation to the needle, the functional member being configured to perform hypodermic procedure function; and wherein the point protector is configured for disengaging from the functional member in the protective position.

23. The puncture needle assembly of claim 22, wherein the point protector comprises an engagement portion that is biased outwardly against the functional member in the inactive position, and which is biased inwardly out of engagement with the functional member in the protective position.

24. The puncture needle assembly of claim 23, wherein the engagement portion of the point protector is in engaged association with the needle in the protective position.

25. The puncture needle assembly of claim 24, wherein the engagement portion comprises an elastic ring for the frictional engagement with the functional member and for the inward biasing of the engagement portion.

26. The puncture needle assembly of claim 24, further comprising a second tube mounted around the needle and defining a groove configured and disposed for receiving the engagement member for the engagement of the engagement member with the needle.

27. The puncture needle assembly of claim 1, wherein the vessel is a syringe or a test tube.

28. The puncture needle assembly of claim 1, wherein the body portion is detachably mountable to the parenteral fluid vessel.

29. The puncture needle assembly of claim 1, wherein the body portion comprises Luer cone.

30. The puncture needle assembly of claim 1, wherein the tube has a wall thickness of less than 0.05 mm.

* * * * *